United States Patent
Yahav et al.

(10) Patent No.: US 8,435,343 B2
(45) Date of Patent: May 7, 2013

(54) BONE GRAFT MATERIAL AND USES THEREOF

(75) Inventors: Amos Yahav, Doar-Na Menashe (IL); Amir Kraitzer, Herzlia (IL)

(73) Assignee: Augma Biomaterials Ltd., Pardes Chana—Karkur (IL)

( * ) Notice: Subject to any disclaimer, the term of this patent is extended or adjusted under 35 U.S.C. 154(b) by 156 days.

(21) Appl. No.: 12/867,302

(22) PCT Filed: Feb. 19, 2009

(86) PCT No.: PCT/IL2009/000195
§ 371 (c)(1), (2), (4) Date: Aug. 12, 2010

(87) PCT Pub. No.: WO2009/104187
PCT Pub. Date: Aug. 27, 2009

(65) Prior Publication Data
US 2010/0312355 A1  Dec. 9, 2010

Related U.S. Application Data

(60) Provisional application No. 61/064,170, filed on Feb. 20, 2008.

(51) Int. Cl.
*C04B 11/00* (2006.01)

(52) U.S. Cl.
USPC ............. 106/772; 106/35; 106/690; 106/691; 423/309; 423/311; 606/92; 623/16.11; 424/423

(58) Field of Classification Search ................... 106/690, 106/691, 35, 772; 423/309, 311; 606/92; 623/16.11; 424/423
See application file for complete search history.

(56) References Cited

U.S. PATENT DOCUMENTS

| 5,281,265 | A | 1/1994 | Liu |
| 6,620,169 | B1 * | 9/2003 | Peterson et al. ................ 606/93 |
| 2003/0167093 | A1 | 9/2003 | Xu et al. |
| 2007/0059281 | A1 | 3/2007 | Moseley et al. |

FOREIGN PATENT DOCUMENTS

| WO | WO 00/27316 | 5/2000 |
| WO | WO 00/45734 | 8/2000 |
| WO | WO 02/05861 | 1/2002 |
| WO | WO 2005/105170 | 11/2005 |

(Continued)

OTHER PUBLICATIONS

International Preliminary Report on Patentability Dated Sep. 2, 2010 From the International Bureau of WIPO Re.: Application No. PCT/IL2009/000195.

(Continued)

*Primary Examiner* — Paul Marcantoni

(57) ABSTRACT

Bone graft compositions for repairing bone defects, which are characterized by a chemical composition of cementitious, non-cementitious, highly-resorbable and poorly-resorbable particulate substances, and further characterized by a specific particle size distribution that includes two or more different ranges of particle size, are disclosed. Further disclosed are articles of manufacturing and unit dosage forms containing the bone graft compositions, methods of repairing bone defects utilizing the bone graft compositions, and processes of preparing the same. Also provided are applicators for applying flowable mixtures formed by mixing a dry composition and a liquid carrier, which are particularly useful for preparing and applying bone graft compositions, as well as methods of using same.

20 Claims, 10 Drawing Sheets

FOREIGN PATENT DOCUMENTS

| WO | WO 2006/082442 | 8/2006 |
|---|---|---|
| WO | WO 2007/046109 | 4/2007 |
| WO | WO 2009/104187 | 8/2009 |

OTHER PUBLICATIONS

Communication Pursuant to Rules 161(1) and 162 EPC Dated Sep. 28, 2010 From the European Patent Office Re. Application No. 09712755.9.

Response Dated Oct. 28, 2010 to Communication Pursuant to Rules 161(1) and 162 EPC of Sep. 28, 2010 From the European Patent Office Re. Application No. 09712755.9.

International Preliminary Report on Patentability Dated May 2, 2008 From the International Bureau of WIPO Re.: Application No. PCT/IL2006/001213.

International Search Report and the Written Opinion Dated Jun. 1, 2010 From the International Searching Authority Re. Application No. PCT/IL2009/000195.

International Search Report and the Written Opinion Dated Dec. 20, 2007 From the International Searching Authority Re. Application No. PCT/IL2006/001213.

Office Action Dated Dec. 7, 2011 From the Israel Patent Office Re. Application No. 207659 and Its Translation Into English.

Communication Pursuant to Article 94(3) EPC Dated May 8, 2012 From the European Patent Office Re. Application No. 09712755.9.

Communication Pursuant to Article 94(3) EPC Dated Oct. 9, 2012 From the European Patent Office Re. Application No. 09712755.9.

* cited by examiner

BONE GRAFT MATERIAL AND USES THEREOF

RELATED APPLICATIONS

This Application is a National Phase of PCT Patent Application No. PCT/IL2009/000195 having International filing date of Feb. 19, 2009, which claims the benefit of U.S. Provisional Patent Application No. 61/064,170 filed on Feb. 20, 2008. The contents of the above Applications are all incorporated herein by reference.

FIELD AND BACKGROUND OF THE INVENTION

The present invention, in some embodiments thereof, relates to novel compositions, unit dosage forms, articles of manufacturing and methods of repairing bone defects and, more particularly, to bone graft compositions that are characterized by controlled, pre-determined setting, curing and bio-resorbability rates and hence can be beneficially utilized for repairing bone defects. The invention also relates to an applicator particularly useful for preparing and applying bone graft compositions.

The rapid development of surgery allows carrying out bones and joints operations such as, for example, orthopedics or maxillofacial surgery including surgical removal of cysts, foci of suppuration and malignant bone tumors. These medical procedures often results in voids, gaps and other bone defects. Other examples of bone defects include those resulting, for example, from compression fractures, high-energy trauma, peri-articular fractures, cranial-maxillo facial fractures, osteoporotic reinforcement (i.e. screw augmentation) and periodontal reconstruction.

Dentistry is an exemplary field in which repairing bone defects is necessary in addition to dental implants, for replacing missing teeth. When a person experiences teeth loss due to trauma or other circumstances, or suffers from periodontal disease, loss of interproximal crestal alveolar bone is one of the conditions which the practitioner must deal with. This bone loss may further result in the loss of a person's interproximal or papillary oral tissue between the corresponding teeth and may cause a bone defect that is very unappealing aesthetically, as well as difficult to restore. Without the proper regeneration of this bone defect, any replacement tooth is likely to be mal-positioned, out of proportion, shape and form, and lack interproximal tissue for a natural appearance.

Depending on the cause and/or location of the various possible bone defects within the body, the volume of the defect can vary, but may, in some cases, reach more than 6 cubic centimeters Since natural bone healing is limited to small cavities and spans long time periods in terms of daily activity, larger bone defects often need to be filled by bone replacement materials which act as temporary fillers, offering a lattice or scaffold upon which natural bone is slowly built. These materials may be liquid, pasty or solid, and are mostly classified by their source: natural or artificial, a feature which invariably influences the biocompatibility of these materials.

Natural bone replacement materials, known as transplants or grafts, include endogenous or exogenous bone fragments. In endogenous bone grafting (autograft), the graft is harvested from a "donor site" in the patient's own body. Autografts are generally the best grafting technique and usually result in the greatest regeneration of missing bone, since the bone is 100% compatible with the patient's body. Although endogenous bone material is highly valuable due to its osteogenic (bone forming), osteoconductive (providing an inert scaffold on which osseous tissue can regenerate bone), and osteoinductive (stimulating cells to undergo phenotypic conversion to osteoprogenitor cell types capable of formation of bone) properties, it is only available in very limited amounts, and thus several surgical procedures are usually necessary to obtain the necessary bone mass from several donor sites. These repetitive surgical procedures pose severe disadvantages to this otherwise beneficial technique.

Exogenous bone graft may be derived from either a human donor (allograft), after undergoing rigorous tests and sterilization, or from an animal source (xenograft), most commonly bovine, after being specially processed to make it biocompatible and sterile. In both cases the exogenous bone acts as a "filler" until the patient's body replaces it with its own natural bone. Unfortunately, exogenous grafts have low or no osteogenicity, increased immunogenicity and a much faster resorption compared to autogenous bone. In clinical practice, fresh allografts are rarely used because of immune response and the risk of transmission of disease. The frozen and freeze-dried types are osteoconductive but are considered to be only weakly osteoinductive at best. Freeze-drying diminishes the structural strength of the exogenous graft and renders it unsuitable for use in situations in which structural support is required. In practice, exogenous bone transplant is often not successful.

Some of the most significant advances in biomaterial research over the last 30 years have been in the field of bone graft substitutes, also termed synthetic grafts or alloplastic grafts, which use inert, man-made synthetic materials that mimic natural bone. Examples of synthetic bone implant and/or bone filler materials include, but are not limited to, metals (for example, special steels, noble metals, platinum or titanium, often used in the replacement of joints) ceramic materials (for example, alumina, glass-ceramics or hydroxylapatite ceramics), calcium phosphate, calcium sulfate and more.

While natural bone grafts are preferable in terms of biocompatibility, they are less practical, especially in the treatment of large cavities, and using synthetic grafts may in fact avoid the additional surgical operations needed to obtain enough natural bone mass.

The type of the synthetic bone replacement material of choice is often dictated by the size, type and location of the bone cavity.

Resorbable bone replacement materials (otherwise termed biodegradable, bioerodable, or bioabsorbable) include materials that are broken down and gradually absorbed or eliminated by various processes in the body. These materials are used as temporary support media or as osteoconductive bone grafts, temporarily filling bone cavities and allowing the body itself to compensate, in the course of time, the defect with living bone material. The exact degree of resorbability is preferably selected such that the rate of resorption at the recipient bone site will match the rate of natural bone growth.

Non-resorbable bone replacement materials are used in bone implantation or "bone augmentation" when the bone cavity is too large to be ever replaced naturally, for example following surgical operations, or when replacing lost teeth. These bone implants must themselves be secured to a supporting bone. Occasionally, the use of non-resorbable bone replacement materials has to be supplemented by the use of resorbable bone replacement materials. For example, in dentistry, when the loss of teeth or periodontal disease results in the loss of the root bone, the potential dental implant site in the upper or lower jaw does not offer enough bone volume or quantity to support the dental implant. Hence, before the placement of bridges or, more commonly, dental implants, supporting bone and/or tissue must be re-grown. This procedure, known as Guided Bone Regeneration (GBR), is accomplished using bone grafts and biocompatible membranes that prevent tissue growth on or around the implant. A bone graft normally takes at least four to six months to heal, before a dental implant can be placed thereon or therein.

One of the most common substances utilized in repairing bone defects in general, and in dental applications, in particular, is hydroxylapatite (HA), $Ca_5(PO_4)_3(OH)$ or $Ca_{10}(PO_4)_6(OH)_2$. Hydroxylapatite is a mineral component found in bones and teeth, and is therefore characterized by the required biocompatibility. Hydroxylapatite, however, often causes irritation of the surrounding bone material. HA, having an approximate resorption time period of 18-36 months is used as a compromise between a highly resorbable and a poorly resorbable material.

Gypsum, for example, is a very soft mineral composed of calcium sulfate dihydrate, $CaSO_4 \cdot 2H_2O$. This form is referred to in the art as calcium sulfate. Heating gypsum at above approximately 150° C. partially dehydrates it to obtain calcium sulfate hemihydrate, $CaSO_4 \cdot \frac{1}{2}H_2O$, is a substance in which the molecular ratio of water molecules to anhydrous calcium sulfate is 1:2, commonly known as "calcined gypsum" or "Plaster of Paris". When calcium hemihydrate is mixed with water at ambient temperatures, it crystallizes into a strong gypsum crystal lattice in an exothermic reaction. Gypsum also has an anhydrous form, termed anhydrous calcium sulfate or calcium sulfate anhydrate, $CaSO4$, which is produced by further heating of the calcium sulfate hemihydrate to above approximately 180° C. Anhydrous calcium sulfate reacts slowly with water to return to the dihydrate form.

In a pure water system, the solubility of these different types of calcium sulfate ranges from about $1.0 \times 10^{-2}$ M to about 4.0×10-2 M (at 25° C.). The anhydrate form, however, is a very hard crystal (hardness rating of 3.5, according to the Mohs Hardness Scale, and a relative density of about 3.0, and has an extremely low dissolution rate in water, even when finely ground, rendering it impractical for in vivo applications. In practice, the anhydrate form is mainly used as a desiccant.

Calcium sulfate compositions are also widely used in bone treatment, and in GBR procedures. Calcium sulfate was first used by Dreesman to obliterate bone cavities caused by tuberculosis in 1893. In 1959, Peltier became the first American to report on the use of calcium sulfate as a bone-graft substitute. The strong crystal structure obtained upon a reaction of the calcium sulfate hemihydrate with water renders it highly suitable for casting into sheets, sticks and molds. This feature attributes to its wide spread use in various applications such as setting broken bones (see, for example, U.S. Pat. No. 3,746,680), in dental GBR for filling small volume cavities (see, for example, U.S. Pat. No. 6,224,635) or in the preparation of dental molds (see, for example, U.S. Pat. No. 4,526,619). Combined with natural or synthetic polymers, calcium sulfate hemihydrate is used for the controlled release of medicaments or pesticides (see, for example, U.S. Pat. No. 6,030,636) or as an implant having a controlled resorption rate in vivo for stimulating bone growth (see, for example, U.S. Patent Application No. 2004/0254259, and U.S. Pat. Nos. 4,192,021 and 4,381,947). In addition, U.S. Patent application Nos. 20020110541, 20020071827 and 20030050710, and U.S. Pat. Nos. 7,371,408, 7,371,409 and 7,371,410, teach bone graft substitute compositions based on various forms of calcium sulfate.

U.S. Pat. No. 6,224,635 teaches that when calcium sulfate hemihydrate dissolves in vivo it elevates the local calcium ion concentration in the surrounding tissue. Then, the newly formed calcium ions react with body fluids to cause local precipitation of calcium phosphate bone mineral in the new soft granulation tissue that is formed around the calcium sulfate as it dissolves and recedes. Since the calcium phosphate is stable in vivo, it provides a matrix for the formation of new in-growing bone tissue, although this process is quite unpredictable.

Unfortunately, the calcium sulfate hemihydrate form is not suitable for the treatment of large cavities due to its expansion properties during setting, which cause pain to the patients. Furthermore, it is characterized by a high dissolution rate and inherently by a fast resorption by the human bone, usually within two to seven weeks, depending upon the particular surgical site. Such a fast absorption renders the calcium sulfate hemihydrate impractical for use in the treatment of large bone cavities, since it cannot be retained at the bone site for long periods of time and is resorbed faster than it can be replaced by new bone, thereby reducing its value to both patient and practitioners in fields such as orthopedics or maxiofacial surgery [ArunK. Garg, D. M. D in Bones biology, Harvesting, Grafting for dental implant. Quintessence publication Ed-1].

The calcium sulfate dihydrate form has acceptable expansion properties. However, its use in repairing bone defects is limited since it has no cementitious properties. Thus, while calcium sulfate dihydrate is often used as surgical cement, additional components are often required so as to achieve the desired cementitious effect. U.S. Pat. No. 5,281,265, for example, teaches that a calcium ion can react with a citrate ion to form a less soluble calcium citrate salt, thus forming cement. Hence, while calcium sulfate dihydrate can theoretically fill large bone cavities, the obtained structures are not stable and invariably break. In fact, there is only limited practical healing success when using calcium sulfate dihydrate in the treatment of large bone defects.

Clearly, the use of the currently available biocompatible synthetic compositions for filling large bone cavities suffer severe disadvantages, such as irritation of the surrounding bone material, poor resorbability, low stability and high expansion, which result in pain and discomfort to the patient and a possible leaking out of the filling material or even a loss of the implant.

WO 2007/046109, of which one of the present inventors is a co-inventor, and which is incorporated by reference as if fully set forth herein, teaches bone grafting compositions which comprise flakes made of a mixture CSH and CSD, which exhibit both the cementitious and binding properties of CSH and the strength and longer resorption period of the rigid CSD and tricalcium phosphate (TCP) granules.

WO 2000/045734 describes a composite, which can be used for filling in bone voids, and which comprise various forms of calcium sulfate hemihydrate, calcium sulfate dihydrate, or combinations thereof.

U.S. Pat. No. 5,281,265 discloses a bone cement material comprising calcium sulfate components, wherein the interaction of a calcium-containing cementing component and a setting component produces a calcium-containing cement which has reduced solubility in water relative to the calcium-containing cementing component. Useful cementing components taught therein are calcium sulfate dihydrate, calcium sulfate hemihydrate and anhydrous calcium sulfate. The cement taught therein can be dried after its preparation, and broken into particles, to form suitable sized particles such as granules.

WO 2000/027316 refers to surgical cement, composed mainly of a calcium sulfate salt, for example calcium sulfate dihydrate, calcium sulfate hemihydrate, anhydrous calcium sulfate and mixtures thereof. The cement taught therein can be used in combination with an implant to repair a bone defect. U.S. Patent Application No. 2003/167093 relates to a bone replacement material based on combination of calcium phosphate compounds, comprising at least two fillers with different in vivo dissolution rates, wherein the compound with the higher dissolution rate will dissolve and create pores for bony ingrowth, and whereas the compound with the lower dissolution rate will still provide strength and toughness reinforcement to the composition, and will only dissolve at a later stage, when more bony material has been formed to support the bone structure, to create additional pores.

WO 2008/094585 provides a method for facilitating bone repair by providing calcium sulfate hemihydrate particles, wherein at least 50% of the particles have a diameter of 50 to 500 nanometer, mixing the particles with an aqueous solution to obtain a paste, applying the paste to an area of bone in need of repair, and allowing the paste to set.

SUMMARY OF THE INVENTION

The present invention, in some embodiments thereof, relates to novel compositions, unit dosage forms, articles of manufacturing and methods of repairing bone defects and, more particularly, to bone graft compositions that are characterized by controlled, pre-determined setting, curing and bio-resorbability rates and hence can be beneficially utilized for repairing bone defects. The invention also relates to an applicator particularly useful for preparing and applying bone graft compositions.

As demonstrated in the Examples section that follows, the present inventors have designed and successfully prepared and practiced several novel unique compositions for bone augmentation, which include various specific combinations of calcium sulfate in different solid hydrate forms (also known as phases), which can, for example, harden in aqueous environment in a relatively short setting time without compromising patient comfort. For example, it has been shown that a particular calcium sulfate phase combination and a particular particle size distribution ratio provided a bone grafting composition characterized by a unique setting time, rigidity and resorption period of the resulting bone graft. In another example, a bone graft composition which includes reinforcing materials which are currently used as dental and orthopedic bone grafts together with a matrix of calcium sulfate as defined herein have been prepared. These compositions provide strong hybrid bone graft materials which are pliable, exhibit short setting times and a very rigid yet highly porous scaffold for bone grafts. These bone graft compositions produce structures which are less brittle than those produced by the known reinforcing materials due to the calcium sulfate matrix that provides the compositions with the desired rigidity.

The present invention, in some embodiments thereof, therefore relates to bone graft compositions, which utilize a mixture of a cementitious substance and a non-cementitious substance, and further utilize a unique particle size distribution of the particles of each of these substances, such that the composition comprises at least two different particle size ranges of the non-cementitious material. The unique particle size distribution of the compositions described herein, imparts to the compositions the desired properties demonstrated and described herein, and renders such compositions highly beneficial for bone augmentation procedures.

Thus, according to one aspect of embodiments of the present invention there is provided a bone graft composition which comprises a plurality of particles of a cementitious substance and a plurality of particles of a non-cementitious substance, said plurality of particles of said non-cementitious material being characterized by at least two non-overlapping ranges of particles size, the composition being characterized by a particle size distribution according to formula I:

$$T = a_0 S_0 + a_1 S_1 + a_2 S_2 + a_3 S_3 + a_4 S_4 + \ldots + a_i S_i + \ldots + a_n S_n \quad \text{Formula I}$$

wherein:

T is the particle size distribution of the composition;

$S_0$ is a particle size range of the cementitious substance;

$a_0$ is a percentage by weight of the particles of the cementitious substance of the total weight of the composition;

i is an integer ranging from 1 to n;

$S_1, S_2, S_3, \ldots S_i$ are each a particle size range of the non-cementitious substance;

at least two of the $S_1, S_2, S_3, \ldots S_i$ are non-overlapping particle size ranges;

$a_1, a_2, a_3, \ldots a_i$ are each a percentage by weight of the particles of the non-cementitious substance having the $S_1, S_2, S_3, \ldots S_i$ particle size range of the total weight of the composition, the cementitious substance and the non-cementitious substance being selected such that upon contacting a mixture of both the substances with an aqueous solution, a biocompatible concrete is formed.

According to some embodiments of the invention, $S_0$ ranges from 0 μm to 500 μm;

$a_0$ ranges from 40 weight percents to 60 weight percents of the total weight of the composition; and a sum of $a_1, a_2, a_3, \ldots a_i$ ranges from 40 weight percents to 60 weight percents of the total weight of the composition.

According to some embodiments of the invention, n=4; $S_1$ ranges from 800 μm to 1600 μm; $S_2$ ranges from 500 μm to 800 μm; $S_3$ ranges from 0 μm to 500 μm; and $S_4$ ranges from 0 μm to 100 μm.

According to some embodiments of the invention, $S_0$ ranges from 0 μm to 100 μm; each of $a_1$ and $a_3$ ranges from 15 weight percents to 18 weight percents of the total weight of the composition; and each of $a_2$ and $a_4$ ranges from 7 weight percents to 10 weight percents of the total weight of the composition.

According to some embodiments of the invention, the cementitious substance includes calcium sulfate hemihydrate (CSH).

According to some embodiments of the invention, the non-cementitious substance is selected from the group consisting of a highly-resorbable substance, a poorly-resorbable substance and a combination thereof.

According to some embodiments of the invention, the non-cementitious highly-resorbable substance includes calcium sulfate dihydrate (CSD).

According to some embodiments of the invention, the poorly-resorbable substance is selected from the group consisting of beta-tricalcium phosphate (β-TCP), hydroxylapatite (HA), bovine-derived hydroxylapatite, porous coralline hydroxylapatite, calcified algae, synthetic particulate glass ceramic, bioactive glass, autogenic bone shavings, allogeneic cancellous bone, irradiated cancellous allogeneic bone, anorganic bovine bone, composites of polymer and calcium hydroxide and any combination thereof.

According to some embodiments of the invention, the cementitious substance includes calcium sulfate hemihydrate (CSH) and the non-cementitious includes calcium sulfate dihydrate (CSD).

According to some embodiments of the invention, the cementitious substance includes calcium sulfate hemihydrate (CSH) and the non-cementitious includes calcium sulfate dihydrate (CSD) and beta-tricalcium phosphate (β-TCP).

According to some embodiments of the invention, $S_0$ ranges from 0 μm to 100 μm; $a_0$ is about 50 weight percents of the total weight of the composition; n=4; $S_1$ ranges from 800 μm to 1600 μm; $S_2$ ranges from 500 μm to 800 μm; $S_3$ ranges from 0 μm to 500 μm; $S_4$ ranges from 0 μm to 100 μm; each of $a_1$ and $a_3$ is independently about 16.5 weight percents of the total weight of the composition; and each of $a_2$ and $a_4$ is independently about 8.5 weight percents of the total weight of the composition.

According to some embodiments of the invention, the concrete is characterized by a setting time which ranges from 1 minute to 1.5 minutes.

According to some embodiments of the invention, the concrete is being pliable and malleable for a time period of from 2 minutes to 4 minutes.

According to some embodiments of the invention, the composition presented herein is capable of forming a cured concrete.

According to some embodiments of the invention, the cured concrete is characterized by a porosity that ranges from 40% to 60% by volume.

According to some embodiments of the invention, the cured concrete is characterized by a resorption period that ranges from 4 to 10 weeks.

According to some embodiments of the invention, the cured concrete is characterized by a compressive strength that ranges from 7 MPa to 15 MPa.

According to some embodiments of the invention, the cured concrete is characterized by an elastic modulus that ranges from 500 MPa to 1000 MPa.

According to another aspect of embodiments of the present invention, there is provided a bone grafting applicator containing therein the bone draft composition presented herein.

According to another aspect of embodiments of the present invention, there is provided a bone grafting applicator for preparing the biocompatible concrete formed by mixing the bone graft composition presented herein and an aqueous solution, and for applying the biocompatible concrete to a bone defect, the applicator comprising:

a cylindrical tube containing the bone graft composition presented herein and formed with an opening at one end thereof;

a piston assembly including a piston moveable within the cylindrical tube, and a piston rod extending through the opposite end of the cylindrical tube and terminating in a finger-piece disposed externally of the cylindrical tube for moving the piston in opposite directions towards and away from the opening in the one end of the cylindrical tube; and a tubular head having one end dimensioned to be removably applied to the one end of the cylindrical tube to communicate with the opening therein, and an opposite end closed by a removable cap;

the arrangement being such that, upon removal of the cap, the piston may be moved from a first position to a second position away from the opening in the cylindrical tube to draw the aqueous solution into the cylindrical tube and to mix with the bone graft composition therein to produce the biocompatible concrete, and the piston may be then moved towards the opening from the second position to a third position to force at least a portion of the aqueous solution, and further, upon removal of the tubular head, the piston may be t moved towards the opening from the third position to thereby force the biocompatible concrete via the opening to the site of a bone defect.

According to some embodiments of the invention, the cylindrical tube is marked with the first, second and third positions.

According to some embodiments of the invention, the one end of the tubular head to be removably applied to the cylindrical tube is of a larger diameter than the opposite end of the tubular head to removably receive the cap.

According to some embodiments of the invention, the opposite end of the cylindrical tube is formed with laterally-extending finger-pieces externally of the cylindrical tube cooperable with the finger-piece of the piston assembly to facilitate moving the piston within the cylindrical tube.

According to some embodiments of the invention, the cylindrical tube is constructed for containing the bone graft composition, and the tubular head is constructed for drawing the aqueous solution therethrough to thereby mix the aqueous solution with the bone draft composition and form the concrete.

According to some embodiments of the invention, the applicator contains a unit dosage form of the bone graft composition presented herein.

According to another aspect of embodiments of the present invention, there is provided a bone graft composition unit dosage form which includes a therapeutically effective amount of the bone graft composition presented herein, which is sufficient to fill a bone defect.

According to some embodiments of the invention, the therapeutically effective amount ranges from 0.3 grams to 20 grams.

According to some embodiments of the invention, the therapeutically effective amount ranges from 0.5 grams to 1.5 grams.

According to some embodiments of the invention, the therapeutically effective amount of the bone graft composition is contained within a bone drafting applicator.

According to some embodiments of the invention, the applicator is as described herein.

According to another aspect of embodiments of the present invention, there is provided a method of repairing a bone defect, which includes:

contacting the bone graft composition presented herein with the aqueous solution, to thereby form the concrete; and applying the concrete to the site of the bone defect, thereby repairing the bone defect.

According to some embodiments of the invention, the method of repairing a bone defect further includes shaping the concrete in the site of the bone defect.

According to some embodiments of the invention, the method of repairing a bone defect further includes allowing the concrete to set and cure, to thereby form a cured concrete.

According to some embodiments of the invention, the contacting and the applying are performed by means of a bone grafting applicator.

According to some embodiments of the invention, the bone grafting applicator is as described herein.

According to some embodiments of the invention, the aqueous solution is selected from the group consisting of water and saline (9% NaCl in water).

According to another aspect of embodiments of the present invention, there is provided an article of manufacturing which includes a packaging material and the bone graft composition presented herein, packaged within the packaging material and identified in print, in or on the packaging material, for use in repairing a bone defect.

According to some embodiments of the invention, the plurality of particles of the cementitious substance and the plurality of particles of the non-cementitious substance are packaged together within the packaging material.

According to some embodiments of the invention, the plurality of particles of the cementitious substance and the plurality of particles of the non-cementitious substance are packaged individually within the packaging material.

According to some embodiments of the invention, the article of manufacturing further includes the aqueous solution, wherein the aqueous solution and the plurality of particles are packaged individually and separately within the packaging material.

According to some embodiments of the invention, the article of manufacturing further includes human readable instructions to contact the bone graft composition with the aqueous solution prior to applying the composition to a site of the bone defect.

According to some embodiments of the invention, the article of manufacturing includes at least one unit dosage form of the bone graft composition.

According to some embodiments of the invention, the dose of the composition in each of the at least one unit dosage form individually ranges from 0.5 grams to 1.5 grams.

According to some embodiments of the invention, the unit dosage form is packaged within a bone grafting applicator.

According to some embodiments of the invention, the bone grafting applicator is as described herein.

According to another aspect of the present invention, there is provided an applicator for preparing a flowable mixture of a dry composition with a liquid carrier, and for applying the flowable mixture to a receiver site, the applicator includes:

a cylindrical tube for receiving the dry composition and formed with an opening at one end thereof;

a piston assembly including a piston moveable within the cylindrical tube, and a piston rod extending through the opposite end of the cylindrical tube and terminating in a finger-piece disposed externally of the cylindrical tube for moving the piston in opposite directions towards and away from the opening in the one end of the cylindrical tube; and a tubular head having one end dimensioned to be removably applied to the one end of the cylindrical tube to communicate with the opening therein, and an opposite end closed by a removable cap;

the arrangement being such that, upon removal of the cap, the piston may be moved from a first position to a second position away from the opening in the cylindrical tube to draw the liquid carrier into the cylindrical tube and to mix with a dry composition contained within the cylindrical tube to produce the flowable mixture, and the piston may be then moved towards the opening from the second position to a third position to force at least a portion of the liquid carrier, and further, upon removal of the tubular head, the piston may be moved towards the opening from the third position to thereby force the flowable mixture via the opening to the receiver site.

According to some embodiments of the invention, the cylindrical tube is marked with the first, second and third positions.

According to some embodiments of the invention, the one end of the tubular head to be removably applied to the cylindrical tube is of a larger diameter than the opposite end of the tubular head to removably receive the cap.

According to some embodiments of the invention, the opposite end of the cylindrical tube is formed with laterally-extending finger-pieces externally of the cylindrical tube cooperable with the finger-piece of the piston assembly to facilitate moving the piston within the cylindrical tube.

According to some embodiments of the invention, the cylindrical tube is constructed for receiving the dry composition, and the tubular head is constructed for drawing the liquid carrier therethrough to thereby mix the liquid carrier with the dry composition.

According to some embodiments of the invention, the cylindrical tube contains the dry composition.

According to some embodiments of the invention, the dry composition is a bone graft composition and the liquid carrier is an aqueous solution to be mixed with the bone graft composition to thereby form a biocompatible concrete as the flowable mixture to be applied to a bone defect as the receiver site, the applicator being a bone grafting applicator.

According to some embodiments of the invention, the bone graft composition is as presented herein.

According to another aspect of embodiments of the present invention, there is provided a method of applying a flowable mixture of a dry composition with a liquid carrier to a receiver site, the method includes:

placing an applicator as described herein, having the dry composition contained within the cylindrical tube, the piston at the first position, and the removable cap being removed, in the liquid carrier;

while the applicator is placed in the liquid carrier, moving the piston to the second position, to thereby draw the liquid carrier into the cylindrical tube;

shaking the cylindrical tube, so as to mix the dry composition and the liquid carrier, to thereby produce the flowable mixture;

moving the piston to the third position so as to force at least a portion of the liquid carrier;

removing the tubular head; and moving the piston towards the opening from the third position, to thereby force the flowable mixture via the opening to the receiver site, thereby applying the flowable mixture to the receiver site.

According to some embodiments of the invention, the method further includes, prior to shaking the cylindrical tube, applying the removable cap onto the tubular head.

According to some embodiments of the invention, the method further includes, subsequent to the shaking, removing the removable cap from the tubular head.

According to some embodiments of the invention, the dry composition is a bone graft composition, the liquid carrier is an aqueous solution and the flowable mixture formed by mixing the bone graft composition and the aqueous solution is a biocompatible bone graft concrete, the method being for applying the concrete to a bone defect.

According to some embodiments of the invention, the method is for repairing the bone defect.

According to some embodiments of the invention, the bone graft composition is as presented herein.

According to another aspect of the present invention, there is provided a process of preparing the bone graft composition presented herein, the process includes:

providing a plurality of non-cementitious coarse particles having an average particle size that ranges from 0 to 1600 µm;

dividing the plurality of non-cementitious coarse particles into the $S_1, S_2, S_3, \ldots S_i$;

providing the plurality of particles of the cementitious substance in the $S_0$; and mixing the $S_0$ and the $S_1, S_2, S_3, \ldots S_i$ according to the formula I.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The words "optionally" or "alternatively" are used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

It is expected that during the life of a patent maturing from this application many relevant methods, uses and compositions will be developed and the scope of the terms methods, uses, compositions and polymers are intended to include all such new technologies a priori.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 6A-D are scanning electromicrographs at different magnifications, taken at different locations of a cured sample of formulation A1, an exemplary bone graft composition according to some embodiments of the invention, in its post-activation and post-curing form, whereas FIG. 6A is taken from a core location at 50-fold magnification and FIG. 6B of the same location taken at 500-fold magnification, and FIG. 6C is taken from a peripheral location at 50-fold magnification and FIG. 6D of the same location taken at 2000-fold magnification, whereas FIG. 6A and FIG. 6C show an overall rough and uneven microstructure of the bulk structure, exhibiting large amorphous pores (pore diameter ranging from 300 µm to 800 µm), and whereas at higher magnifications FIG. 6B shows the micro-pores between CSD crystals, and FIG. 6D shows the needle-shaped strongly intergrown crystals of CSD which determine the porous fine microstructure comprising pores of various sizes and shapes;

FIGS. 7A-C are scanning electromicrographs of cured samples of formulation B, an exemplary bone graft composition according to some embodiments of the invention, wherein FIG. 7A is a micrograph at a magnification of 1500-fold, FIG. 7B is a micrograph at a magnification of 2500-fold and FIG. 7C is a micrograph at a magnification of 5000-fold, showing a porous and irregular microstructure;

FIGS. 8A-B are photographs of an exemplary applicator device according to some embodiments of the invention, composed of four basic elements, namely a cylindrical tube, a piston, an applicator's head and a cap fabricated from certified biocompatible raw materials that withstand gamma radiation according to ISO standards, designed to contain the bone graft composition according to the present embodiments, and eventually apply the same, wherein FIG. 8A shows an applicator for a small dose of 0.5 cc (about 0.63 grams) of dry bone graft composition, and FIG. 8B shows a larger size applicator containing 1 cc (about 1.25 grams) of the composition;

DESCRIPTION OF THE PREFERRED EMBODIMENTS

Figure 1:
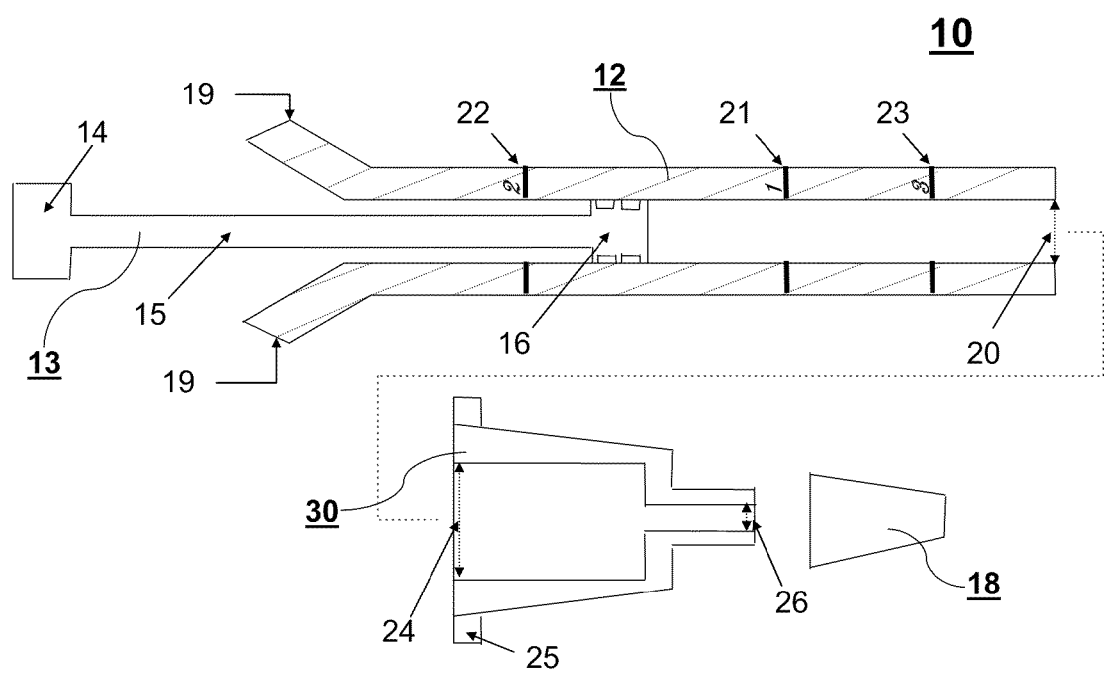
FIG. 1 presents a schematic illustration of an exemplary bone graft applicator 10 according to some embodiments of the invention, suitable for storing, preparing and applying a bone graft composition, according to some embodiments of the invention, wherein the dry composition is contained inside tube 12, plugged on one side by piston 16 and other the other side by head 30 fitted with cap 18 at aperture 20, and further marked with first line 21, second line 22 and third line 23, each signifying a position of piston 16 relative to aperture 20.

The present invention, in some embodiments thereof, relates to novel compositions, unit dosage forms, articles of manufacturing and methods of repairing bone defects and, more particularly, to bone graft compositions that are characterized by controlled, pre-determined setting, curing and bio-resorbability rates and hence can be beneficially utilized for repairing bone defects. The invention also relates to an applicator particularly useful for preparing and applying bone graft compositions.

The principles and operation of the present invention may be better understood with reference to the figures and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, calcium sulfate is known in the art as an augmentation filler material for bone defects, however, its use in practice is limited, mostly due to its inappropriate mechanical properties and rapid resorption, leading to inconsistent results. This limitation is mitigated to some extent by use of rigid materials in the form of granules or plates, which provide slower resorption periods. Nevertheless, in practice, these materials do not provide the required binding properties, plasticity or pliability during application.

Medical grade calcium sulfate is a biocompatible, bioresorbable, and a clinically versatile ceramic for use in bone repair, or cavitary bone defects. Due to its safety, formability and its complete resorption followed by new bone formation, calcium sulfate has been used as a filling material for bone defects in regenerative techniques.

The hemihydrate form of calcium sulfate ($CaSO_4 \cdot \frac{1}{2}H_2O$; abbreviated herein as CSH), is derived from the common mineral gypsum, calcium sulfate dihydrate ($CaSO_4 \cdot 2H_2O$; abbreviated herein as CSD). Adding water in proper quantities to CSH causes CSD to form during setting while it crystallizes into a strong gypsum crystal lattice in a mild exothermic reaction (no tissue damage has been reported). Heating gypsum at above approximately 150° C. partially dehydrates it to obtain CSH. Calcium sulfate also has an anhydrous form, termed anhydrous calcium sulfate or calcium sulfate anhydrate ($CaSO_4$; abbreviated herein as CSA) which is produced by further heating CSH to above approximately 180° C. CSA reacts slowly with water to afford CSD.

In typical bone regeneration techniques the bone cavity is filled by a mixture of CSH powder and water (or water solution) and a resulting paste, exhibiting good handling properties and formability, is left to harden in situ to the dihydrate form. Other practices use CSD pre-hardened grafting materials, presented in granule forms, or block forms, which are carried into the defected site. Calcium sulfate is rapidly and completely resorbed, creating a calcium-ion rich milieu in the area of implantation. These calcium ions may provide some stimulation to osteoblasts, which may account for some of the positive results reported with the material. It has been shown that calcium sulfate acts as more than a simple space filler that prevents soft tissue ingrowth; in fact, as it dissolved, calcium sulfate leaves a consistent latticework of hydroxylapatite calcium-phosphate mineral, which was found to be stable in the long term and to act as an osteoconductive trellis for new bone formation. It was also found to promote the formation of blood vessels, which is extremely important for bone formation.

However, despite its efficiency, the potential applications are limited by the rapid in vivo resorption and the brittleness of calcium sulfate, thus, the use of calcium sulfate is associated with inconsistent results. CSD is not suitable in itself as a bone replacement material, since it does not adhere to the defected area. This form of calcium sulfate is characterized by a slow resorbability rate relative to the hemihydrate form. When it is present in the form of granules it is preferably used in repairing bone defects when combined with additional cementitious materials, for example polymeric materials. CSH is not suitable for the treatment of large cavities due to its expansion properties during setting, which are painful to the patients. In addition, CSH is characterized by a high dissolution rate and inherently by a fast resorption by the human bone, usually within two to seven weeks, depending upon the particular surgical site. Such fast absorption rates render CSH impractical for use in the treatment of large bone cavities, since it cannot be retained at the bone site for long periods of time and is resorbed faster than it can be replaced by new bone, thereby reducing its value to both patient and practitioners in fields such as orthopedics or maxiofacial surgery.

The mineral phase of bone is mainly composed of natural hydroxylapatite (HA). Therefore bio-cements based on synthetic HA and other calcium salts, phosphates and sulfates, are among the most investigated materials for dental and orthopedic applications in reconstructive surgery. Biological source of HA include bovine HA or coral HA. HA bioceramics are widely employed as bone substitute materials with good results, for example, in the treatment of periodontal osseous defects and alveolar ridge augmentation. Highly crystalline HA is resorbed slowly over decades, rather than years, hence, most HA implant materials are osteoconductive. However, when large blocks are used, the ability of osteoprogenitor cells to migrate may be compromised, and fibrous connective tissue may result. In addition, HA was found to be too brittle and difficult to handle.

Calcium phosphate cements are used in orthopedics as well as orbital bone support in plastic surgery. Calcium phosphate ceramics are biocompatible, bioactive materials generally available as blocks or granules of dense or porous ceramics. The material is soluble and gradually dissolves in the body, seeding new bone as it releases calcium and phosphate ions into the biological medium. Calcium phosphate bone substitutes, especially in macro-porous forms, show biodegradability and osteoconduction properties, and biphasic calcium phosphate (BCP) ceramics, an association of HA and beta-tricalcium phosphate (β-TCP), have proved to be efficient bone substitutes that respond well to material resorption/bone substitution events. Tricalcium phosphate was first used as a bone graft substitute in 1920. It has two crystal forms, α-TCP and β-TCP that differ in their mechanism and kinetics of resorption. Whereas hydroxylapatite has calcium to phosphate molar ratio of 1.67, TCP has calcium to phosphate molar ratio of 1.5. TCP is less crystalline than hydroxylapatite, and therefore, more soluble. Implants that contain TCP are both biocompatible and osteoconductive, but because of its relative solubility it is used in situations where structural support is less important. Biphasic calcium phosphates of varying HA/β-TCP ratios can be prepared by mechanical mixing of b-TCP and HA powders in desired quantities or by chemical methods producing calcium-deficient apatite forms (CDA). The final macro-porous BCP ceramic depends on its HA/β-TCP ratio and the BCP obtained by sintering. Such BCP ceramics are now currently used for bone filling in spinal, tumoral, orthopedic and periodontal applications. Although the use of calcium phosphate cement and calcium phosphate pellet has been successful, handling of these forms of implants is quiet difficult. Macro-porous blocks have proved brittle and difficult to sculpt and do not fit tightly to the surface of bone defects, and granules are difficult to handle and to keep in place after implantation.

Presently used pre-hardened grafting materials are presented in granule forms, or block forms, which are carried into the defected surgical site. This, in turn, presents poor manipulation characteristics which compromise the healing of the bone and requires a skilful clinician in most cases. The facts the granules are not interconnected to form stable cements are of great disadvantage. Many attempts have been made to solve the above noted problems for having the ability to shape, formalize and hardened it as needed in situ. Among the materials considered, plaster of Paris, collagen, different type of calcium phosphate groups, polylactates and polyacrylate cements; none of this materials offered an acceptable comprehensive solution.

The present inventors have envisioned that a hybrid material, which would exhibit both the cementitious and binding properties of CSH as well as the strength and longer resorption period of presently known calcium sulfate-based bone grafting products, could be efficiently utilized for forming bone graft compositions while overcoming the limitations associated with the currently available bone graft compositions. As discussed hereinabove, this concept was presented in WO 2007/046109, of which one of the present inventors is a co-inventor, where compositions comprising flakes made of a mixture of CSH, CSD and CSA are described.

While conceiving the present invention, it was suggested that a novel composite material or bone graft composition for repairing bone defects, and for bone augmentation in general, which can afford a strong yet porous solid having a relatively short resorption period compared to other bone grafting products, can be derived from a mixture of cementitious and non-cementitious substances, formulated in a particular distribution of particle size, so as to achieve a concrete, in a form of a cementitious paste, that allows a workable time frame for application, which is long enough to allow satisfactory positioning of the paste in the grating site, and at the same time has a short setting time resulting in a short curing period.

It was further conceived that an effective cementitious bone augmentation material, formed in a particular particle shape and size distribution, can be produced from CSH and CSD in unique combination thereof, with CSA or devoid of CSA, and can also be reinforced by beta-TCP ceramic, HA, and other bone grating/augmentation materials currently available. Such compositions would be superior to presently used bone grafting compositions by being free of polymeric additives or special chemical accelerators. Such bone grafting compositions can be formulated and shaped so as to allow their packing into simple mechanical applicators. The bone graft compositions can be activated in the applicator prior to their application by pumping water, saline or other aqueous solutions into the applicator, and be ready for immediate use by means of a simple technique. The activated composition can then be applied by the practitioner into the surgical site, shaped and formed as required, and let harden in situ for several minutes.

While reducing the present invention to practice, the present inventors have prepared bone graft compositions according to a specific particle size distribution of cementitious and non-cementitious substances, which was found to posses highly beneficial combination of mechanical properties such as pliability, setting and curing time, and a highly porous cured (solid) structure, leading to desirable, predictable and reproducible optimal results.

While further reducing the present invention to practice, bone graft compositions that are basically composed of the hemihydrate and dihydrate forms of calcium sulfate, reinforced in some cases by more rigid and/or less resorbable bone grafting/augmentation materials, have been prepared and characterized.

Thus, according to one aspect of the present invention there is provided a bone graft composition which includes particles of a cementitious substance as well as particles of a non-cementitious substance, which are provided in a characteristic particle size distribution, as further defined and detailed hereinbelow.

As used herein, the phrase "bone graft composition" describes an essentially dry mixture of substances, typically in the form of particulate matter (powder, particles, granules, aggregates, shavings and the likes), which can be mixed with a suitable liquid to form a viscous flowable matter that can be placed in a bone defect, such as a void, a gap or a crack, so as to fill the bone defect and let to set and cure. Bone graft compositions therefore include substances which are suitable for such medical procedures, as described herein.

Herein throughout, the terms "material" and "substance" are used interchangeably.

According to embodiments of the invention, the cementitious substance and the non-cementitious substance are selected such that upon contacting a mixture thereof with an aqueous solution, a biocompatible concrete is formed.

The terms "cement" or "cementitious", as used herein, refer to a dry, granular and/or powdered substance or a mixture of dry, granular and/or powdered substances, which can act as a binder upon activation with a liquid, typically water or another aqueous solution. Upon activation of cement by contacting the cement with water or another aqueous solution, cement affords a cementitious paste, as defined hereinbelow. The cementitious paste sets (solidifies) and hardens (cures) to form a rigid mass as a result of a chemical process known as a hydration reaction. Thus, a cementitious substance can bind non-cementitious substances and materials, as defined herein, mixed therewith upon activation to form a rigid composite mass known as cured concrete.

An exemplary cementitious substance that is highly suitable for use in the context of embodiments of the invention includes CSH, as described herein.

Additional exemplary cementitious substances that can be suitable for use in the context of embodiments of the invention include, but are not limited to, calcium hydroxide, various forms of calcium silicates, various natural and fabricated pozzolans, fly ash, silica fume, various polymers and combinations thereof.

The term "non-cementitious" as used herein, describes a substance which does not set and hardens upon the addition of a liquid. Particles of non-cementitious substances are commonly mixed with cementitious substances and a solvent, typically water or other aqueous solutions, to form fortified or reinforced rigid composite mass, commonly known as concrete, as defined herein. For example, calcium sulfate hemihydrate (CSH) is a cementitious substance, while calcium sulfate dihydrate (CSD) is not. However, mixtures of CSH and CSD can set, harden and thus form rigid solid mass upon activation with water or other aqueous solutions.

An exemplary non-cementitious substance that is highly suitable for use in the context of embodiments of the invention includes CSD, as described herein.

Additional exemplary non-cementitious substances that can be suitable for use in the context of embodiments of the invention include, but are not limited to, various minerals of calcium, hydroxylapatite, particulate glass ceramic and bioactive glass, various composites of polymer and calcium minerals and combinations thereof.

As used herein, the term "concrete" or the phrase "cementitious paste", which are used herein interchangeably, refer to a wet paste which comprises one or more cementitious substances (cement), such as calcium sulfate hemihydrate, one or more non-cementitious substances in a variety of particle sizes, water or another aqueous solution, and optionally other additives. As defined herein, a concrete can be substantially pliable and malleable between the time it starts to set (solidify) and the time it hardens (cures) after mixing with water and placement (rest). The setting or hydration reaction commences as a result of contact between cement and water. The setting process, characterized by a setting time, as defined herein, leads to the binding of all other non-cementitious components together, eventually forming a composite reinforced rigid mass, referred to herein as cured concrete.

As used herein, the phrase "aqueous solution" refers to a liquid mixture containing water as a major solvent, among other minor solvents and solutes.

According to some embodiments of the present invention, the aqueous solution can be water, purified water, medical grade water for injection or saline (0.9% NaCl in water, typically purified and sterile). Such biocompatible solutions can afford biocompatible concretes.

As used herein, the term "biocompatible" refers to a material, substance, concrete or composition, which is substantially non-toxic, does not cause severe adverse biological effect, or lethality in an animal when administered to a subject at a pharmaceutically acceptable amounts, doses and/or rates.

The phrase "setting time", as used herein, refers to the time period which passes from the moment an aqueous solution has been added to cement and mixed therewith to the onset (commencement) of hardening or setting process of the cementitious paste (concrete). The completion of a setting process produces a cured solid, or cured concrete, as defined herein.

The terms "malleability" or "pliability", as used interchangeably herein, refer to a mechanical property of a substance which can be deformed plastically without fracture. Specifically, these terms refer to a material's ability to deform under compressive stress, which is often manifested by the material's ability to be molded into any shape without cracking or forming fractures. Accordingly, a pliable or malleable substance is one that exhibits the mechanical properties of malleability or pliability.

As used herein, the phrase "cured concrete" refers to the solid mass which forms by cements (e.g., cementitious material or paste) and optionally other components after setting and curing. A cured concrete can be characterized by its morphology or other internal macro- or micro-structure features (such as voids, cracks, porosity and crystallinity), and by its chemical and physical characteristics (such as hardness, compressive strength, elastic modulus, chemical stability, resorbability and degradability). A cured concrete is defined herein regardless of other substances which may be present in its voids and pores (such as unbound particles, water or other solvents).

According to some embodiments of the invention, the cementitious substance is calcium sulfate hemihydrate (CSH). Once wetted and set, CSH is essentially transformed to calcium sulfate dihydrate (CSD). Both CSD and CSH are bio-resorbable, as defined herein.

As used herein, the term "resorbable" refers to a substance which can undergo resorption, as this term is defined hereinbelow. When the resorption process takes place in a biologic system, the substance is referred to as "bioresorbable".

The term "resorption", as used herein, describes a loss of a substance through chemical, biological and/or physiologic processes. Typically, this term is used herein and in the art to describe such a process which involves decomposition of a substance by, e.g., chemical or physical break-down, such as dissolution, hydrolysis and/or phagocytosis, which may be followed by absorption and/or excretion of the breakdown products by the body via, for example, metabolism. The term resorption is therefore often referred to herein and in the art as "bioresorption". Accordingly, the phrase "resorption period", as used herein, refers to the time period of the resorption process.

The terms "highly-resorbable" and "poorly-resorbable" are used herein to divide the substances which are suitable for use in the bone graft composition presented herein into two groups according to their approximate resorption time period as known in the art. A "highly-resorbable" substance, according to some embodiments of the present invention, is such that exhibits an approximate resorption time period of 1-2 months or about 4-10 weeks, while a "poorly-resorbable" substance exhibits an approximate resorption time period of more than 10 weeks. In essence, a poorly-resorbable substance can be such that is essentially non-resorbable (infinite resorption time period), at least in terms of the life expectancy of the subject in which the graft is formed.

For a non-limiting example, calcium sulfate, and particularly CSD, is a highly-resorbable substance, having an approximate resorption time period of 1-2 months.

Non-limiting examples of poorly-resorbable substances include the following materials listed with their approximate resorption time in parentheses, beta-TCP (4-12 months), micro-porous hydroxylapatite particulate (18-36 months), bovine-derived hydroxylapatite with synthetic peptide (18-36 months), calcified algae (6-18 months), synthetic particulate glass ceramic (bioactive glass, 18-24 months), autogenic bone shavings (3-7 months), allogeneic cancellous bone (6-15 months), irradiated cancellous allogeneic bone (4-12 months), inorganic bovine bone (15-30 months), porous anorganic crystal (4-10 months), porous coralline hydroxylapatite (5-7 years) and composite of micro-porous Bioplant HTR polymer coated with calcium hydroxide (10-15 years).

According to some embodiments of the invention, the non-cementitious substance can be a highly-resorbable substance, a poorly-resorbable substance, as defined herein or a combination thereof.

When the non-cementitious substance is in the form of particles of various sizes, a combination of the highly-resorbable substance and the poorly-resorbable substance can be in the form of a mixture of particles, each comprised of one of the substances, or in the form of coated and partially coated particles wherein some of the particles are made from the poorly-resorbable substance and coated or partially coated with the highly-resorbable substance, and/or vice-versa, and any combination thereof.

In some embodiments of the invention, the non-cementitious highly-resorbable substance is calcium sulfate dihydrate (CSD), and in some embodiments the poorly-resorbable substance can be, for non-limiting examples, beta-tricalcium phosphate (β-TCP), hydroxylapatite (HA), bovine-derived hydroxylapatite, porous coralline hydroxylapatite, calcified algae, synthetic particulate glass ceramic, bioactive glass, autogenic bone shavings, allogeneic cancellous bone, irradiated cancellous allogeneic bone, inorganic bovine bone, composites of polymer and calcium hydroxide and any combination thereof.

The choice of poorly-resorbable substance will depend on the specific clinical need; hence, for clinical procedures where the bone graft is required to linger for extended periods of time, the selected poorly-resorbable substance would be such that exhibits a longer bio-resorption time period. Furthermore, a poorly-resorbable substance which lingers longer in the bone graft, would impart its rigidity and strength to the entire bone graft structure due to the fact that is erodes slower than highly-resorbable substances.

As used herein and in the art, a particle size distribution, or PSD, of a powdered or granular material, is a list of values in a mathematical function that defines the relative amounts of particles present in the material, typically sorted according to the particles size. A PSD of a sample can be represented by the sum of the products of relative amounts, typically represented by their percentage of the whole sample, and the various particle size bins, typically represented in a particle size range which populates each bin and denoted by the upper and lower limits of particle sizes. In other words, a particle size distribution describes the relative portion of each particle size in a plurality of particles in the powdered or granular material.

Hence, the PSD of the bone graft compositions presented herein can be represented by formula I as follows:

$$T = a_0 S_0 + a_1 S_1 + a_2 S_2 + a_3 S_3 + a_4 S_4 + \ldots + a_i S_i + \ldots + a_n S_n \quad \text{formula I}$$

wherein:

T is the particle size distribution (PSD) of the composition;
$S_0$ is a particle size range of the cementitious substance;
$a_0$ is a percentage by weight of the particles of the cementitious substance of the total weight of the composition;
i is an integer ranging from 1 to n;
n is an integer which is larger than 1, and typically larger than 2, larger than 3, or larger than 4.
$S_1, S_2, S_3, \ldots S_i$ are each a particle size range of the non-cementitious substance;
$a_1, a_2, a_3, \ldots a_i$ are each a percentage by weight of the particles of the non-cementitious substance of the total weight of the composition.

In some embodiments, the particles of the cementitious substance are characterized by a certain particle size range, denoted as $S_0$.

The particles of the non-cementitious substances are characterized as having at least two non-overlapping particle size ranges, as defined hereinafter. The particle size ranges of the non-cementitious substance can be all different from the particle size range of the cementitious substance, or, alternatively, one of the particle size ranges of the non-cementitious substance can be the same, or can overlap, the particle size range of the cementitious material used, as detailed hereinbelow.

As used herein, the term "non-overlapping" describes overlap of less than 20%, less than 15%, less than 10%, less than 8%, less than 5%, less than 4%, less than 3%, less than 2%, less than 1%, less than 0.5%, less than 0.1% overlap of the different particle size ranges, and even a substantial non-overlap (0% overlap).

According to some embodiments of the invention, the cementitious substance is present as a fine powder, denoted $S_0$ having a particle size ranging from 0 μm to 500 μm. The relative amount of the cementitious substance in the bone graft composition, denoted $a_0$, ranges from 40 weight percents to 60 weight percents of the total weight of the composition, while the particles of the non-cementitious substance(s) constitute the rest of the composition, namely a sum of $a_1, a_2, a_3, \ldots, a_i, \ldots a_n$ $$\left( \text{i.e.,} \sum_{i=1}^{n} a_i = a_1 + a_2 + a_3 + \ldots + a_{n-1} + a_n \right)$$

ranges from 40 weight percents to 60 weight percents of the total weight of the composition.

The cementitious substance is aimed at binding the particles of the non-cementitious substance(s) and hence it is advantageous to utilize particles of this substance which are small enough to enter crevices, niches, voids and space in and between larger particles.

Hence, according to some embodiments, the particle size bin of the cementitious substance denoted $S_0$, is populated by particles of size that ranges from 400 μm to 0 μm, from 300 μm to 0 μm, from 200 μm to 0 μm, from 100 μm to 0 μm, from 50 μm to 0 μm or 10 μm to 0 μm.

Alternatively, the particle size bin of the cementitious substance denoted $S_0$, is populated by particles of size that ranges from 400 μm to 300 μm, from 300 μm to 200 μm, from 200 μm to 100 μm, from 100 μm to 50 μm or from 50 μm to 10 μm.

Further alternatively, the particle size bin of the cementitious substance denoted $S_0$, is populated by particles of various combinations of the aforementioned particle size ranges.

According to some embodiments of the invention, the cementitious substance is present as a fine powder, denoted $S_0$ having a particle size ranging from 0 μm to 100 μm.

According to some embodiments of the invention, the particles of the non-cementitious substance(s) populate at least two bins, such that n is 2 or more.

In some embodiments, the particles of the non-cementitious substance(s) populate 3, 4, 5, 6, 7, 8, 9 and even 10 bins, such that n is an integer from 2 to 10. Thus, the particles of the non-cementitious substance can have 2, 3, 4, 5, 6, 7, 8, 9 or 10 different, non-overlapping, size ranges.

According to some embodiments of the invention, a selected and pre-defined size distribution of particles of various and substantially non-overlapping size ranges (at least two non-overlapping size ranges) can be characterized by a large surface area. A relatively large surface area produces a fast growing cementitious matrix, which means that the particles adsorb water more rapidly and therefore, given sufficient amount of an aqueous solution, requires less time to set and cure.

Exemplary particle size ranges include, but are not limited to, particles of sizes that range from 2000 µm to 1000 µm and from 1000 µm to 500 µm in cases of two non-overlapping size ranges; particles of sizes that range from 1800 µm to 900 µm, from 1200 µm to 600 µm and from 600 µm to 200 µm in cases of three size ranges having two non-overlapping size ranges; and particles of sizes that range from 1600 µm to 800 µm, from 800 µm to 500 µm, from 500 µm to 0 µm and from 100 µm to 0 µm in cases of four size ranges having at least two non-overlapping size ranges.

In some embodiments, the particles of the non-cementitious substance(s) populate at four bins, namely n=4.

In some embodiments, the non-cementitious substance have particle size ranges from 1600 µm to 800 µm in the particle size bin denoted $S_1$, from 800 µm to 500 µm in the particle size bin denoted $S_2$, from 500 µm to 0 µm in the particle size bin denoted $S_3$, and from 100 µm to 0 µm in the particle size bin denoted $S_4$. As can be seen in this embodiment, $S_1$, $S_2$ and $S_3$ are non-overlapping particle size ranges, and $S_4$ overlaps with $S_3$ in the particle range from 100 µm to 0 µm, which comes to increase the population of the smallest particles in the PSD.

The relative amounts of each particle size range can vary according to the specific characteristics of the desired concrete. Hence, $a_1$, $a_2$, $a_3$, ... $a_i$ which represent these relative amounts in formula I, can take any value, and as presented hereinabove, the sum of all can range, according to some embodiments, from 40% to 60% of the total composition.

In some embodiments, when the particles of the non-cementitious substance are partitioned into four particle size bins, as described hereinabove (n=4), each of $a_1$ and $a_3$ ranges from 15 weight percents to 18 weight percents of the total weight of the composition, and each of $a_2$ and $a_4$ ranges from 7 weight percents to 10 weight percents of the total weight of the composition.

As demonstrated in the Examples section that follows below, several bone graft compositions have been prepared and practiced successfully.

For example, in the family of compositions referred to herein as formulation A family, the cementitious substance is calcium sulfate hemihydrate (CSH) and the non-cementitious is calcium sulfate dihydrate (CSD). In a specific and non-limiting example of a bone graft composition belonging to the formulation A family referred to herein as formulation A1, the PSD can be represented by formula I, defined hereinabove, with the following variables:

$S_0$ ranges from 0 µm to 100 µm;
$a_0$ is about 50 weight percents of the total weight of the composition;
n=4;
$S_1$ ranges from 800 µm to 1600 µm;
$S_2$ ranges from 500 µm to 800 µm;
$S_3$ ranges from 0 µm to 500 µm;
$S_4$ ranges from 0 µm to 100 µm;
each of $a_1$ and $a_3$ is independently about 16.5 weight percents of the total weight of the composition; and
each of $a_2$ and $a_4$ is independently about 8.5 weight percents of the total weight of the composition.

As demonstrated in the Examples section that follows, an exemplary bone grafting (bone augmentation) composition according to the present embodiments, which is provided herein and referred to as formulation A1, is also known as Bond Bone™ This novel composition is a self-reinforced and highly-resorbable bone graft material which is based on two forms of highly pure medical grade calcium sulfate, namely calcium sulfate hemihydrate (CSH) and calcium sulfate dihydrate (CSD) which are formulated at a uniquely controlled particle size distribution. This composition is intended for example, for use as bone void filler. It exhibits both volume maintenance and structure rigidity properties that allow it to function as a superior scaffold for bone regeneration. The composition is easy to use, and does not require membrane coverage after its application. It is applied by itself using standard bone regeneration techniques; or mixed with other suitable bone filling agents to prevent particle migration in an osseous defect; and to provide a resorbable barrier over other bone graft materials.

Bone graft compositions belonging to the formulation A family, which are based on calcium sulfate, are useful in clinical cases wherein the bio-resorption is required to be short, in the order of 1-2 months.

In another example, in the family of compositions referred to herein as formulation B family, the cementitious substance is calcium sulfate hemihydrate (CSH) and the non-cementitious includes a combination of calcium sulfate dihydrate (CSD) particles and particles of poorly-resorbable substances, some of which are coated and/or partially coated with a layer of CSD, as presented hereinabove and exemplified in the Examples section that follows hereinbelow.

Bone graft compositions belonging to the formulation B family, which are based on calcium sulfate which is a highly-resorbable substance, combined with poorly-resorbable substances, are useful in clinical cases wherein the bio-resorption is required to be longer than 1-2 months.

In a specific and non-limiting example of a bone graft composition belonging to the formulation B family, referred to herein as formulation B1, the poorly-resorbable substance is beta-tricalcium phosphate (β-TCP), and the PSD can be represented by formula I, defined hereinabove, with the following variables:

$S_0$ ranges from 0 µm to 100 µm;
$a_0$ is about 50 weight percents of the total weight of the composition;
n=4;
$S_1$ ranges from 800 µm to 1600 µm;
$S_2$ ranges from 500 µm to 800 µm;
$S_3$ ranges from 0 µm to 500 µm;
$S_4$ ranges from 0 µm to 100 µm;
each of $a_1$ and $a_3$ is independently about 16.5 weight percents of the total weight of the composition; and
each of $a_2$ and $a_4$ is independently about 8.5 weight percents of the total weight of the composition.

According to an aspect of embodiments of the present invention, there is provided a process of manufacturing the bone graft composition presented herein, which includes:
providing a plurality of non-cementitious coarse particles having a wide range of particle sizes (e.g., from 1 to 2000 µm or from 1 to 1600 µm);
dividing this plurality of non-cementitious coarse particles into individual particle size bins, namely $S_1$, $S_2$, $S_3$, ... $S_i$ as defined hereinabove, and according to some embodiments of the invention, having at least two of $S_1$, $S_2$, $S_3$, ... $S_i$ be non-overlapping particle size ranges;
providing the plurality of particles of a cementitious substance in the form of $S_0$; and
mixing the particle bins $S_0$ and $S_1$, $S_2$, $S_3$, ... $S_i$ according to the formula I.

This rudimentary grinding and sieving process begins with a fresh preparation of the cementitious substance. When using poorly-resorbable substances, the coarse granules thereof can be premixed with the cementitious substance and wetted to afford cement-coated granules, which are then grinded and sieved to afford the various particle size bins.

In embodiments based on calcium sulfate, the grinding and sieving process begins with a fresh preparation of CSH which is then transformed to fresh CSD. When using poorly-resorbable substances, the coarse granules thereof are premixed with CSH and wetted to afford CSD-coated granules, which are then grinded and sieved to afford the various particle size bins.

Detailed descriptions of such processes of manufacturing the compositions presented herein are provided in the Examples section that follows below.

The bone graft compositions presented herein, which are essentially dry granular compositions, are meant for use as concrete or cementitious paste, as these terms are defined hereinabove. Thus, the selected particle size distribution of the particles of calcium sulfate in a selected ratio of hydration forms offers the desired characteristics which are suitable for bone grafting procedures. Typically, such procedures begin with the hydration of the composition with water, saline or other aqueous solutions, followed by a spontaneous setting stage (e.g., hydration reaction) which affords a transient pliable paste that allows good handling properties for enough time to complete the bone repair/augmentation procedure, and eventually ends in a well positioned rigid (cured) structure. From a mechanical point of view, the strength of the cured graft is determined in the first 4-6 minutes following the initiation of the hydration reaction. The cured concrete in reinforced by the relatively large particles of the non-cementitious substance(s) (e.g., CSD) which are bonded together by the precipitation of cementitious substance (e.g., CSH).

Prior to their use, the bone graft compositions presented herein are in the form of a dry powder. In order to activate the composition and commence the setting reaction of the composition, an aqueous solution is introduced to the dry powder to thereby afford a cementitious paste. Hence, according to some embodiments of the present invention the concrete, or cementitious paste, which is formed when the dry composition is mixed with (contacted) and wetted (hydrated or activated) by an aqueous solution, is characterized by a setting time which ranges from 1 minute to 1.5 minutes.

According to some embodiments of the invention, the cementitious paste allows the practitioner to insert the paste into the site of the bone defect by remaining pliable and malleable for a time period of from 2 minutes to 4 minutes.

The particular combination of hydration forms (phases) of calcium sulfate in a particular particle size distribution ratio provides a unique bone graft composition which exhibits an optimal setting and curing time, porosity, rigidity and bio-resorption period.

Thus, according to some embodiments of the invention, the bone graft compositions are capable of forming a cured concrete, as this term is defined hereinabove, which can be characterized by porosity, compressive strength, elastic modulus and a resorption period, which are some of the parameters by which cured concrete is most commonly analyzed, characterized and standardized.

The particle size variation and the irregularity of the particles increase the surface area available between the particles of the cementitious substance (e.g., CSH) and the particles of the non-cementitious substance(s) (e.g., CSD). During the setting reaction, looser (less packed) particles will a cured into a more porous solid (having more voids). Hence, the rigid structure which is obtained from the bone graft compositions presented herein exhibits a porosity of approximately 50% by volume, namely 50% of the solid is void and can be filled with the aqueous physiological media. This property determines the degradation period as well as the biologic quality of the scaffold while implanted in bone tissue, as macro-pores permits bone cells proliferation, adherence and angiogenesis, and micro-pores allow growth factors diffusion.

The cured concrete which can be formed by the bone graft compositions presented herein can be characterized by porosity which ranges from 40% to 60% by volume. Alternatively, the porosity of the cured concrete formed by the compositions presented herein is about 20%, about 30%, about 40%, about 50%, about 60% and about 70%. The porosity, according to some embodiments of the present invention, can be estimated by "true density", which is the density of a porous solid that is defined as the ratio of its mass to its true volume. The means by which the true density of cured concretes which are formed from the compositions presented herein, are presented in the Examples section which follows hereinbelow.

The unique properties of the ingredients of the present compositions determine the degradation period that subsequently determines the graft resorption rate. The bone graft compositions provided herein are further characterized by an average bio-resorption rate that corresponds and matches to bone generation rate at the selected bone defect. While osteoid formation occurs within the period of 6-10 weeks, bio-resorption period of existing bone grafting compositions known in the art is 4-6 weeks, which is too short in most cases, whereas the cured concrete which can be formed by the bone graft compositions presented herein, such as formulation A1 and formulation B1 (see, Examples section hereinbelow) is characterized by a resorption period of 4 to 10 weeks.

As discussed hereinabove, the selection of the poorly-resorbable substance(s) and the particle size range thereof affect the bio-resorption time period of the cured concrete that forms therefrom. Thus, the type and presence of a poorly-resorbable substance is selected depending on the clinical purpose and requirements. For example, compositions for graft which require 4-12 months to resorb may include beta-TCP; grafts which require 18-36 months to resorb may include micro-porous hydroxylapatite particulate; grafts which require 6-15 months to resorb may include allogeneic cancellous bone; and grafts which require 5-7 years to resorb may include porous coralline hydroxylapatite.

According to some embodiments of the present invention, the bone graft compositions described herein are formulated so as to produce a reinforced matrix, or a composite bone grafting material, which combines good handling properties with short setting time and final rigidity, which is less brittle than the solids obtained by presently known compositions.

Thus, in some embodiments, the compressive strength of the cured concrete obtained from bone graft compositions comprising highly-resorbable substances ranges from 7 MPa to 10 MPa, and the elastic modulus thereof ranges from 500 MPa to 700 MPa.

Accordingly, in some embodiments, the compressive strength of the cured concrete obtained from bone graft compositions comprising a combination of highly-resorbable and poorly-resorbable substances ranges from 10 MPa to 15 MPa, and the elastic modulus thereof ranges from 750 MPa to 1000 MPa.

From the bioresorption and stability balance considerations, the cementitious pastes and cured concretes, which are made from the bone graft compositions presented herein, offer optimal bio-resorption rates when exposed to in vivo conditions, such as saliva and blood which affect dissolution rates by hydrolysis and phagocytosis, compared to other calcium sulfate-based bone graft composition that are less stable and tend to be washed away by saliva and blood before completion of the setting reaction.

The cementitious properties of the pastes obtained from the bone graft compositions provided herein are advantageous, providing a self-reinforced material which remains hard and intact in the presence of blood and saliva, thus preserving the three dimensional space throughout the healing period.

As demonstrated in the Examples section that follows below, and without being bound to any particular theory, the combination between the unique particle size distribution (PSD) and the non-cementitious substance(s) (e.g., CSD) to cementitious substance (e.g., CSH) ratio, determined the kinetics of the setting reaction, thereby reducing the setting time. Consequently, the measured time point when maximum setting temperature was measured (a time/temperature point which indicates the peak of the setting reaction, not to be confused with the "setting time" as defined hereinabove) was 3:34 minutes. The particles of the non-cementitious substance(s) serve as nucleation cores for the crystallization of the cementitious substance in the area surrounding the non-cementitious substance particle, thereby prompting the setting reaction.

Furthermore, the PSD has an important role in determining the strength and degradation by inducing the porosity obtained during the setting reaction, which is far less affected by the presence of blood and saliva, compared to other bone graft compositions known in the art.

The aforementioned characteristics of both the cementitious paste and the cured concrete which are afforded by the bone graft compositions presented herein, amount to provide a highly desirable bone repair and augmentation tool in the hands of a practitioner, even if the latter is not highly skilled in the art of preparing and using such compositions.

Thus, according to another aspect of the present invention, there is provided a method of repairing a bone defect, which is primarily based on contacting the bone graft composition presented herein with an aqueous solution as defined hereinabove, to thereby achieve a complete wetting of the composition. A complete wetting of the composition affords a concrete or a cementitious paste. It is noted herein that a complete and uniform wetting of the dry bone graft composition determines the uniformity and consistency of the concrete, and therefore the stage of contacting the composition with the aqueous solution should be given substantial attention. However, this stage should not exceed the time limit of the setting and curing time of the concrete.

Contacting the dry composition and the aqueous solution can be done in any suitable sized vessel, such as a glass, metal or porcelain dish. Alternatively, the specific characteristics of the bone graft compositions presented herein allow the use of specially designed applicator, which can be used also for the wetting stage, as well as for containing dry composition, drawing the aqueous solution to start the wetting process, and applying the freshly formed concrete. A detailed description of such an applicator follows hereinbelow.

The method further includes applying the concrete to the site of the bone defect. The mechanical characteristics of the concrete which can be formed from the bone graft compositions presented herein are such that the cementitious paste can be easily applied directly on the treated site by being flowable and yet stable within a relatively long period of time before the setting reaction is advanced and the paste hardens.

Following the application of the concrete, the method may further include shaping the concrete so as to fill the bone defect as desired; a stage in the methods which is essential for obtaining an effecting bone graft, which is afforded by the characteristic setting time of the compositions presented herein. Shaping the concrete may be achieved by hand or by means of a shaping tool such as a spatula, a spoon, a broad flat blade and the likes.

In cases where the paste is contained in an applicator, as described herein, it can be applied directly from the applicator and even be partially shaped thereby.

The method further includes allowing the concrete to set and cure to thereby form a cured concrete. By allowing it is meant that the shaped concrete in the bone defect is left untouched and moist until it is completely cured, as detailed herein.

In order to assure consistent results from experienced practitioners as well as from inexperienced practitioners, the bone graft composition, according to some embodiments, can be provided as a bone graft composition unit dosage form which includes a therapeutically effective amount of the bone graft composition.

The phrase "unit dosage form", as used herein, describes physically discrete units, each unit containing a predetermined quantity of the bone graft composition, calculated to produce the desired therapeutic effect.

In some embodiments, the unit dosage form comprises a therapeutically effective amount of the bone graft composition.

In the context of the present invention, the phrase "therapeutically effective amount" is used to describe an amount of the bone graft composition which can form a corresponding amount of a cementitious paste with is sufficient to fill a bone defect. Accordingly, there is provided a bone graft composition unit dosage form which includes a therapeutically effective amount of the bone graft composition presented herein, which is measured so as to be sufficient to fill a bone defect having a given void to be filled.

According to some embodiments of the present invention, the therapeutically effective amount can range from 0.3 grams to 20 grams. Alternatively, as demonstrated in the Examples section that follows, a suitable dose for a unit dosage form, which is most commonly used in most dental and mandible bone grafting and augmentation procedures, ranges from 0.5 grams to 1.5 grams. In other cases, the therapeutically effective amount depends on the size of the void or other bone defect to be treated.

According to some embodiments, the therapeutically effective amount of the composition can be contained within a bone grafting applicator, as detained herein.

When describing a composition contained in a bone graft applicator, or a bone grafting cementitious paste being prepared and applied by means of an applicator, it is meant that the bone graft compositions presented herein and the cementitious pastes which can be prepared therefrom can be contained, prepared and applied respectively from any bone grafting applicator known in the art, or any applicator which is suitable for bone grafting procedures.

However, in order to further simplify the use of the bone graft compositions presented herein, in terms of containing the composition (for example, as in the aforementioned dosage unit form), wetting and forming a cementitious paste therefrom, as well as applying the paste, the present inventors have designed and successfully used a unique bone grafting applicator, designed in a cylinder-piston form. Such a design was made possible due to the unique characteristics of the compositions presented herein and the unique cementitious pastes which form therefrom.

The applicator described herein can be used to contain and apply any of the bone graft compositions presented herein, as well as various other presently known bone graft compositions, and in general any flowable pasty mixture, for containing and/or wetting a dry composition which is a precursor of the flowable mixture, or simply for applying the flowable mixture onto any desired site.

Thus, according to another aspect of embodiments of the present invention, there is provided an applicator for preparing a flowable mixture from a dry composition and a liquid carrier, as well as for applying the flowable mixture to a receiver site (e.g., bone repairing site).

The bone grafting applicator, which is particularly useful for preparing a flowable mixture of a dry composition with a liquid carrier, and for applying the flowable mixture to a receiver site, includes:

a cylindrical tube for receiving the dry composition, which is formed with an opening at one end thereof;

a piston assembly including a piston moveable within the cylindrical tube, and a piston rod extending through the opposite end of the cylindrical tube and terminating in a finger-piece disposed externally of the cylindrical tube for moving the piston in opposite directions towards and away from the opening in the one end of the cylindrical tube;

and a tubular head having one end dimensioned to be removably applied to the one end of the cylindrical tube to communicate with the opening therein, and an opposite end closed by a removable cap;

the arrangement of the applicator is such that, upon removal of the cap, the piston may be moved from a first position to a second position, away from the opening in the cylindrical tube, to thereby draw the liquid carrier into the cylindrical tube and to mix it with the dry composition therein, thereby producing the flowable mixture. The piston may also be moved towards the opening from the second position to a third position to force at least a portion of the liquid carrier, and, upon removing the tubular head, may be further moved towards the opening from the third position to thereby force the flowable mixture via the opening and onto the receiver site.

As used herein, the term "flowable" refers to a mixture of insoluble solid particles mixed with a liquid carrier, that is able to flow, such as, for example, a cementitious paste.

FIG. 1 presents a schematic illustration of an exemplary bone graft applicator constructed in accordance with some of the embodiments of the present invention, which may be used for preparing and applying the bone graft compositions presented herein. While the illustrated applicator is particularly useful for such a purpose, it will be appreciated that it could be used for preparing and applying other flowable mixtures constituted of a dry composition mixed with a liquid carrier.

The applicator illustrated in FIG. 1 and denoted applicator 10, includes three main parts: a cylindrical tube, generally designated tube 12, for receiving the dry composition; a piston assembly, generally designated piston assembly 13, for use in mixing the liquid carrier with the dry composition, and for applying the flowable mixture to a receiver site; and a tubular head, generally designated head 30, for use in introducing the liquid carrier into the dry composition within tube 12, and for assuring a good mixture thereof before the mixture is applied to the receiver site. In some embodiments, the liquid carrier is the aqueous liquid to be mixed with the bone graft composition presented herein, hence the dry composition.

Thus, as shown in FIG. 1, tube 12, which receives the dry composition (e.g., the bone graft composition presented herein) is formed with an opening, denoted aperture 20 at one end, for drawing in the liquid carrier (the aqueous solution) to be used for mixing with the dry composition to form a pasty flowable mixture (e.g., the concrete presented herein), which after so formed, is forced through aperture 20 onto the receiver site.

Tube 12 is further formed with three markers identifying various distances from the aperture 20, namely: a first marker, generally designated first line 21, a second marker at a greater distance from aperture 20, generally designated second line 22, and a third marker at a smaller distance from aperture 20, generally designated third line 23. As will be described below, these markers are used for locating the position of piston assembly 13 to facilitate the introduction of the liquid carrier via head 30 for mixing with the dry composition within tube 12, for enhancing the mixture if necessary, and for forcing the mixture out via aperture 20 onto the receiver site.

Tube 12 is further formed with a plurality of laterally-extending finger-pieces 19 at the end opposite to the end of aperture 20, cooperable with piston assembly 13 to move piston assembly 13 to the desired position within tube 12. Piston assembly 13 includes piston 16 moveable within tube 12, and piston rod 15 extending through the end opposite to the end of aperture 20 of the tube 12 and terminating in finger-piece 14 extruding laterally externally of tube 12. Finger-piece 14 is adapted to be engaged by the thumb of a user, while two of the fingers engage finger-pieces 19, in order to facilitate the movement of piston 16 in opposite directions, towards and away from aperture 20 in tube 12.

Head 30 includes a large-diameter end 24 dimensioned to be removably applied to the end of aperture 20 of tube 12 so that the interior of head 30 communicates with aperture 20 formed in tube 12. Preferably, head 30 is formed with a lateral flange, generally designated flange 25 to facilitate its application and removal from end of aperture 20 of tube 12. Head 30 is further formed with a small-diameter end 26, closed by a removable cap, generally designated cap 18.

As will be described more particularly below, the dry composition, such as the bone graft composition presented herein, may be stored within tube 12, between piston 16 and aperture 20 at the end of tube 12, which would be closed by head 30 including cap 18. When the dry composition is to be mixed with the liquid carrier, cap 18 is removed, the small-diameter end 26 of head 30 is immersed in the liquid carrier, and piston 16 is moved from the position marked by first line 21 away from aperture 20 to the position marked by second line 22, thereby drawing the liquid carrier into tube 12 for mixing with the dry composition therein. If desired to enhance the mixture, cap 18 may then be reapplied to head 30 and applicator 10 may be slightly shaken, impacted or vibrated until the desired pasty mixture is produced.

Once the dry composition is thoroughly wetted by the liquid carrier, head 30 may then be removed, and a semi-barrier, such as a static gauze cloth, may be placed over aperture 20 to permit excess of the liquid carrier to be pushed out through the semi-barrier by piston 16 by moving it from its second position towards aperture 20 to its third position marked by third line 23, in order to force excess of the liquid carrier out through aperture 20.

When the pasty mixture is deemed ready for use, piston assembly 13 is used to extrude the pasty mixture out through aperture 20 to the receiver site. It is noted herein that when head 30 is removed, the pasty mixture can be pushed out from an aperture which is sufficiently wide to extrude viscous flowable mixtures such as the pasty mixture that is formed within tube 12. That is made possible due to the cylindrical shape of tube 12, having the width of aperture 20 throughout its length.

Hence, according to some embodiments of the invention, the granulated dry bone grafting compositions presented herein can be packed in an applicator, such as for example a disposable mechanical applicator, while drawing water or another suitable aqueous solution into the applicator's cylindrical tube by means of a retractable piston assembly, to thereby wet and activate the dry composition therein. The setting process commences within the tube of the applicator following the interaction between water or saline and the bone graft composition, resulting in a pliable cementitious paste that allows good handling properties for a time period of about 2-4 minutes. Once the composition is sufficiently wetted, the applicator's head can then be detached and the wide aperture of its tube can be used to apply the resulting thick and viscous cementitious paste into the bone defect site.

Thus, according to another aspect of the present invention, there is provided a method of applying a flowable mixture of a dry composition with a liquid carrier to a receiver site, which includes:

placing an applicator as described hereinabove, having the dry composition contained within the cylindrical tube, the piston at the first position, and the removable cap being removed, in the liquid carrier;

while the applicator is placed in the liquid carrier, moving the piston to the second position, to thereby draw the liquid carrier into the cylindrical tube;

shaking the cylindrical tube, so as to mix the dry composition and the liquid carrier, to thereby wet the dry composition and produce the flowable mixture;

moving the piston to the third position so as to force an excess portion of the liquid carrier;

removing the tubular head; and moving the piston towards the opening from the third position, to thereby force the flowable mixture via the opening to the receiver site, thereby applying the flowable mixture to the receiver site.

Removing the tubular head can be performed prior to or subsequent to any of the shaking and the moving of the piston to the third position.

In order to prevent spillage and splashing, the removable cap may be reapplied onto the tubular head which is placed on the cylindrical tube prior to shaking the applicator. Other means, as described hereinabove, can also be used. The cap alone or the entire head can be removed subsequent to the shaking and wetting process.

As presented hereinabove, in some embodiments of the invention, the dry composition is a bone graft composition, such as the compositions presented herein, the liquid carrier is an aqueous solution, such as water or saline, and the flowable mixture formed by mixing the bone graft composition and the aqueous solution is a biocompatible bone graft concrete. In such embodiments the method described herein is suitable for applying a bone grafting concrete to a bone defect. In these cases, the method can be regarded as a method for repairing a bone defect.

In order to further assist the practitioner, the use of the composition presented herein is made simpler by providing the user a pre-packaged product that can be easily identified and selected from an inventory of products and tools without the need to measure, weight or practice technical skills in order to prepare the composition prior to its use at the time of need.

Hence, according to another aspect of the present invention, there is provided an article of manufacturing that includes a packaging material (e.g., a primary or exterior package) and a bone graft composition as presented herein, which is packaged (e.g., in a secondary package) within the packaging material and identified in print, in or on the packaging material, as a composition for use in repairing a bone defect.

For a "ready to use" article of manufacturing, according to some embodiments of the present invention, the particles of the cementitious substance and the particles of the non-cementitious substance are packaged together (e.g., in secondary packages) within the (e.g., primary) packaging material.

According to other embodiments, the particles of the cementitious substance and the particles of the non-cementitious substance are packaged individually in secondary packages within a primary packaging material. This form of the article of manufacturing allows the skilled practitioner to further control the characteristics of the resulting cementitious paste and cured concrete, as the ratio between the cementitious and non-cementitious particles can be finely tuned to suit the conditions of extraordinary cases.

The article of manufacturing can further include the aqueous solution packaged individually in another secondary package, separately from the dry components of the composition within the primary packaging material.

Alternatively, the composition can be a powder from which the practitioner takes the desired amount for preparing the desired amount of concrete.

The article of manufacturing, according to some embodiments of the invention, can include at least one unit dosage form of the bone graft composition, as unit dosage forms are presented herein. Thus, it can include a single unit dosage form or a plurality of dosage forms individually packaged within the article.

Alternatively, the article of manufacturing can include one or more individually packaged applicators, as provided herein, used as unit dosage forms of the composition presented herein.

Typically a unit dosage form is packaged in a secondary package within a primary package.

The article of manufacturing may include unit dosage forms in various suitable secondary packaging forms, such as bone grafting applicators, blisters, containers, bottles, jars, tubs, sachets, pouches, vials, ampoules, syringes and tubes.

In order to further assure consistent results from experienced practitioners as well as inexperienced practitioners, the article of manufacturing can further include some form of human readable instructions, which explain and illustrate how to contact the bone graft composition with the aqueous solution prior to an application of the resulting concrete.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

Calcium sulfate dihydrate (CSD) precipitated EMPROVE® Ph EUR, BP, E516 pharmaceutical grade powder was obtained from Merck Chemicals Ltd.

TRIHA+® (a bio-active tricalcic phosphate ceramics) was used as 100% Beta-TCP ceramics (β-TCP), provided by Teknimed, S.A.

Cerabone®, a hydroxylapatite ceramic made of purely inorganic granules was purchased from AAP.

Bio-Oss®, the mineral portion of bovine bone was purchased from Geistlich Biomaterials.

Purified water, Ph Eur (CAS 7732-18-5) was purchased from Fluka.

Table 1 presents the abbreviations of materials and formulations used in the experimental section presented herein.

TABLE 1

| Abbreviation | Composition | Trade Name |
|---|---|---|
| CSH | — | Calcium sulfate hemihydrate |
| CSD | — | Calcium sulfate dihydrate |
| CSA | — | Calcium sulfate anhydrate |
| β-TCP | — | beta-tricalcium phosphate |
| A1 | CSH, CSD | Bond Bone ™ |
| A2 | CSH, CSD, CSA | |
| B1 | CSH, CSD, β-TCP | Bond Bone Plus ™ |

Formulation A—General Procedure:

In the first stage CSD is converted to CSH, a portion of the resulting CSH is set aside and the rest of the CSH is rehydrated by immersion in purified water (50% v/w) and mixing for 5 minutes in order to obtain fresh CSD. The wet CSD is left to dry partially for at least 20 minutes on a flat open surface and then heated at low temperatures in order to arrive at a water content of about 20-30% v/w.

This process is performed to ensure the presence of large crystals of CSD, which provide the ability to control the particle size distribution of CSD so as to include relatively large and stable particles. This freshly obtained dried CSD is crumbled to constitute a basic particle size level, which contains the desired maximal particle size of about 1.6 mm (1600 μm), exhibiting an amorphous and irregular morphology.

This crumbled CSD of the basic particle level is further dried by heat (typically 100° C. for 2 hours) and may be further grinded coarsely as needed. The resulting particles are then sieved through a series of mesh-cutoff sieves going from coarse sieve to fine sieve to thereby obtain a series of separated powders of CSD particles characterized by a range of particle size, referred to herein as particle size bins.

The previously obtained CSH is grinded and sieved through a fine mesh to obtain particles of size range of less than 500 μm, in some cases less than 100 μm.

Portions of the various CSD and CSH bins are mixed according to a predetermined ratio to obtain a dry mass of CSD and CSH particles.

The irregularity of the particle forms and the different size distribution, as well as the hydration phase composition, greatly affect the setting time and the performance of the material, as demonstrated hereinbelow.

Formulation A1:

Formulation A1, an exemplary composition according to the embodiments of the invention, was prepared according to the General Procedure presented hereinabove.

CSH was prepared from medical grade CSD by heating 500 grams of CSD in an oven at 150° C. for 8 hours.

A portion of the CSH was sieved by a mesh size of less than 100 μm to obtain particle size bin "E", and set aside.

The remaining major portion of the CSH was immersed in purified water and mixed for 5 minutes to form CSD afresh. The resulting wet paste of fresh CSD was left to set and drain for at least 20 minutes on a flat open surface. The cured and drained cake is broken into chunks of about 1 cm in overall size, and the chunks were dried by heat for about 3 hours in an oven set at 50° C. in order to arrive at a water content of about 20-30% v/w. Thereafter the freshly obtained and dried CSD was milled to the basic particle size level using a Fritsch Pulverisette 14 grinding machine equipped with a 12 blades titanium rotor, and impact blades, which was operated at 12,000 rpm, which is defined as the raw or basic grinding level.

The resulting CSD granules were sieved through a 1.6 mm mesh sieve post-milling, and the sieved particles, characterized by size range of 0-1600 μm, were heated to 100° C. for about 2 hours, or until the weight of the lot was reduced by 30% by weight.

The resulting crude granules were sieved using a stack of sieves of predetermined mesh sizes starting at 800 μm to afford particle size bin "A" corresponding to particle size range of 800-1600 μm, followed by a mesh of 500 μm to afford particle size bin "B" corresponding to particle size range of 500-800 μm, and the particles which passed the 500 μm mesh were collected to thereby constitute particle size bin "C" corresponding to particle size range of 0-500 μm.

The combined remainders of the CSD particles were re-grinded into a fine powder using the same equipment set at 20,000 RPM and equipped with a 2 mm mesh blade rotor, defined as the fine grinding level, to produce particle size bin "D" corresponding to particle size range of 0-100 μm.

Formulation A1 was prepared by admixing particular weighted portions from each particle size bin of CSD, namely "A", "B", "C" and "D", and a portion of fine powder of CSH, namely "E", at a particular ratio as presented in Table 2 below.

In certain cases, CSD can be heated up to 180° C. for one hour to produce CSA, which can be added to the mixture in formulation A2.

Table 2 presents the composition formulation A1 in weight percentage.

TABLE 2

| Particle size bin | Corresponding variable in Formula I | Weight percentage | Particle size range |
|---|---|---|---|
| A | $S_1$ | 16.5% | 800-1600 μm |
| B | $S_2$ | 8.5% | 500-800 μm |
| C | $S_3$ | 16.5% | 0-500 μm |
| D | $S_4$ | 8.5% | <100 μm |
| E | $S_0$ | 50% | <100 μm |

Formulation B—General Procedure:

In another formulation of a bone graft composition for bone augmentation procedures, according to some embodiment of the invention, a cementitious reinforced material is created by using relatively large granules of non-calcium sulfate bone grafting materials, including poorly-resorbable materials, incorporated with calcium sulfate particles composed from specific mixtures of CSH and CSD with or without CSA, prepared in a predefined particle size distribution. The origin of the non-calcium sulfate bone grafting materials may be of commercially available bone augmentation materials such as β-TCP, Cerabone®, Bio-Oss® and the likes. Similar to the compositions stemming from formulation A presented hereinabove, the irregularity of the particle forms and the different size distribution thereof greatly affect the setting time and the performance of the material.

According to some embodiments, the compositions belonging to the family of formulation B are characterized by the presence of particles of either highly-resorbable or poorly-resorbable material(s) (substance). These poorly-resorbable materials are reduced to a coarse particle size (basic particle size level); then mixed with a fine powder of a highly-resorbable cementitious substance, such as CSH; then wetted to initiate cementation (the hydration reaction) to thereby affect the coating of the non-cementitious particles with a coat of the cured cementitious substance, such as CSD. Thereafter the particle size of the coated particles is reduced by grinding followed by sequential sieving of the resulting composite (fully and/or partially coated with a highly-resorbable cured cementitious substance) particles to obtain a predetermined particle size distribution thereof. The resulting composite particles having a predetermined particle size distribution are then mixed again with a fine powder of a highly-resorbable cementitious substance, such as CSH, in a 1:1 ratio, to thereby obtain the composition of formulation B.

Formulation B1:

In this exemplary bone graft composition, referred to herein as formulation B1, the non-calcium sulfate material used was β-TCP, exhibiting a particle size range of 3 mm to 6 mm.

The β-TCP granules (TRIHA+®) were grinded for about 10 seconds per step using a Fritsch Pulverisette 14 grinding machine equipped with a 12 blades titanium rotor only without blades, which was operated at 9,000 rpm to thereby obtain particle bin A. Particle bin B of β-TCP was obtained by using the same grinding machine with impact blades, and fresh β-TCP particles of category bin C were obtained by using the same grinding machine operated at 20000 RPM, using 12 ribs titanium rotor and 2 mm mesh blades. Thereafter, particles from bins A, B, and C were mixed together at equal amounts by weight to thereby constitute bin D.

Bin D was mixed with freshly prepared fine powder of CSH, prepared as described hereinabove for formulation A, at a ratio of 1:0.5 w/w, to thereby constitute bin E.

Bin E was mixed with purified water at a ratio of 1:0.5 w/v and the mixture was allowed to set for 20 minutes, thereby affecting the particles coating.

After allowing the setting reaction to run for 20 minutes, the cured material was crumbled, and uncoated particles from bin A were added and mixed in at a ratio of 1:4 relative to the dry mass used from bin E, to thereby constitute bin F.

Thereafter, the dry particulate mass of bin F was grinded for about 10 seconds using a Fritsch milling machine operating at 9000 rpm and equipped with a 12 ribs titanium rotor and impact blades.

Following the grinding, the material of bin F was dried in an oven set to 100° C. for about one to three hours, or until 10-30% of its weight was lost due to water evaporation. The material was allowed to cool to room temperature and then sieved into different grain sizes varying from 1 μm to 1600 μm, as described for formulation A1 hereinabove, to thereby control and set the particle size distribution with respect to the non-cementitious particles of the composition.

After sieving and verifying the required particle size distribution, the composition of the material was determined by weight percentages, as presented for formulation A1 hereinabove.

At the final stage, CSH (freshly prepared fine powder having a particle size range of 0-100 μm, identical to the material used in the preparation of formulation A1) was added at a ratio of 1:1 by weight (50% by weight of the total weight of the composition).

Characterization of Formulation A1 (Bond Bone™):

The characterization of formulation A1 was carried out in during the bench testing of formulation A1 (Bond Bone™) at the facilities of RMS FOUNDATION, Switzerland and at the facilities of INTERLABOR BELP AG, Switzerland.

Purity:

The goal concentration of trace elements in the calcium sulfate raw material (before setting) is limited to less than 10 ppm of total heavy metals (for example, arsenic, cadmium, mercury and lead). Other metallic elements, such as iron, may also affect the biocompatibility or implant performance and in order to meet USP grade, should not be higher than 100 ppm. Element screening for Pb, Cd, Hg, As and Fe was performed in accordance with F1088 Test Procedure at Interlabor Belp AG (ILB) by inductively coupled plasma (ICP) combined with atomic absorption spectroscopy (AAS), atomic fluorescence spectroscopy (AFS), or without.

Compressive Strength:

Cured samples of bone graft composition, such as the exemplary formulation A1 (Bond Bone™) were prepared according to the pre-application procedure described herein, as well as in the instructional video provided to the practitioner and available on-line (internet sites). The resulting wet and pliable cementitious paste was extruded into cylindrical metallic molds of 9.5 mm (±0.5 mm) in diameter and 9.5 mm (±0.5 mm) height. The molds were tempered at 37° C. from the beginning of the preparation to the extrusion of the specimen. After injection, the molds were covered with a wet tissue and stored at 37° C. for 1 hour. Afterwards the specimens were sanded to the exact height of the molds and then extruded. Each specimen was placed in a cavity of a cell-culture well plate. The well plate was closed with a lid in order to prevent evaporation. After 24 hours at 37° C. the specimens were dried at ambient conditions (21±1° C., 40±5% relative humidity) for 24 hours and in an exsiccator at room temperature for at least 48 hours. The samples were then let to equilibrate to ambient humidity and temperature for at least 24 hours.

Six specimens of each product were tested using Zwick 1475 tensile testing machine set at 0.5 mm/minute feed rate according to DIN 50106 (standard testing of metallic materials; compression test). The maximum compressive strength is reported for each sample, as well as the mean value and the standard deviation. The elastic modulus was determined manually from the stress-strain curves.

Particle Size Distribution:

The particle size distribution of the dry mass of formulation A1 calcium sulfate was analyzed prior to adding an aqueous solution thereto using a sieving method. Stainless steel sieves were stacked on a collecting pan with decreasing mesh sizes from top to bottom. 100 grams (±10 grams) of the specimen were added to the top sieve. The lid was locked and the shaker was started with an amplitude of 1.50 mm for 30 minutes using Retsch AS200 analytical sieve shaker. Collector plate used was Retsch ISO 3310–1200×50 mm (Body 316L, Mesh S-Steel/RF) with mesh sizes 32, 53, 106, 250, 500, 710, 1000, 1400, 2000 μm. Scale used was Mettler Toledo PB3002-L DeltaRange®.

Thereafter the sieves were weighed as follows:

The scale was reset to 0.00 gram;

The sieve and its content were weighed, and the value was recorded as M1 (±0.01 gram);

The content of the sieve was discarded in a collecting vessel and the sieve was tapped moderately on a flat surface upside-down to remove remaining powder;

The empty sieve was weighed, the value was recorded as M2 (±0.01 gram);

The difference M3 was calculated as M1−M2 and recorded;

Once all M3 values had been determined, relative fraction were calculated as M4=M3/($\Sigma$(1−10)M3i) and recorded as M4.

Calcium Sulfate Hydration Form Content:

The relative content of various calcium sulfate hydration forms, or phases, in the bone graft composition according to the present embodiments, such as the exemplary formulation A1, was analyzed prior (dry powder) and after the water-activated setting reaction using quantitative Rietveld refinement analysis of the X-ray powder diffraction (XRD) data. Amorphous fractions were quantified by the internal standard method.

Cured samples were prepared from a dry powder form of the composition according to the procedure described herein, using formulation A1 and saline (0.9% sodium chloride in water) solution as an aqueous solution. The resulting cementitious paste was extruded into cylindrical metallic molds of 9.5 mm (±0.5 mm) in diameter and 9.5 mm (±0.5 mm) height. The molds were tempered at 37° C. from the beginning of the preparation to the extrusion of the specimen. After injection, the molds were covered with a wet tissue and stored at 37° C. for 1 hour. Thereafter the specimens were extruded from the molds, and each was placed in a cavity of a cell-culture well plate. The well plate was closed with a lid in order to prevent evaporation. After 24 hours at 37° C. the specimens were dried at ambient conditions (21±1° C., 40±5% relative humidity) for 24 hours and in an exsiccator at room temperature for at least 48 hours. Three samples of the dry powder form of the composition (prior to adding saline) and three samples of the cured composition were prepared as described hereinbelow, and lithium fluoride (LiF) was added as an internal standard.

0.700 grams (±0.001 gram) of the sample were added to an agate mortar;

0.300 grams (±0.001 gram) of dehydrated LiF were added to the mortar;

The powder was manually homogenized and crushed for 10 minutes with moderate force;

The powder was pressed into aluminum sample holders following the generally accepted rules to ensure good compaction and avoid orientation effects.

XRD diffractometer used was Panalytical X'Pert Pro MPD diffractometer, reflective geometry set at 40 kV, 40 mA generator settings, using CuKα anode, radiation Ni-filtered in the diffracted beam. Optics was fixed divergence slit of ⅛° opening, 10 mm mask, 0.02 rad Soller slits, with 1 revolution per second spinner. Angle range measured: 5-80° 2θ with step size 0.016° 2θ and counting time 60 seconds per step.

XRD data-sets were processed with the Rietveld refinement software FullProf.2k version 4.00. The following templates were used for phase determination: CSD: PDF #04-010-9409, CSH: 01-074-2787, CSA: PDF #04-007-6682, LiF: PDF #04-006-5934. Refined parameters included correction for vertical sample displacement, intensity of sampled background points, scale parameters of all phases, cell parameters of all phases, preferred orientation of all phases, and spherical harmonics to model anisotropic crystallite sizes of all phases. The instrument resolution function and peak asymmetry was determined prior to the data collections with a "NIST SRM 660a-Line Profile LaB6" standard sample. The results were corrected for micro-absorption by calculating a Brindley coefficient for each phase. An estimated average particle radius of 5 μm was used for the calculations.

pH Analysis:

The pH in the immediate environment of a cured form of the bone graft compositions described herein (such as the exemplary formulation A1) during the first 24 hours after application was determined. Analysis of the pH in the immediate environment of cured bone graft material during the first 24 hours after implantation can be used to determine whether complications due to acid release are to be expected.

Cured samples were prepared according to the procedure described in the compression strength test hereinabove. The water pH was measured using a Knick Portamess, KCl electrode pH meter before and after incubation. The solutions of 8-10 samples were mixed in order to obtain enough liquid for the pH measurement. Prior to the pH analysis, the pH meter was 2-point-calibrated at pH 4.01 and 7.00. After incubation, the solutions of all specimens of a product were mixed and cooled to room temperature. The pH of each solution was measured several times.

SEM Analysis of Particle Shape:

The setting process and the mechanical properties of the cementitious paste and the resulting cured material are not only influenced by the chemical composition of the dry powdered composition, but also by the shape and size distribution of the particles of the powder. As presented herein, it was found that a particular particle size distribution and an irregular and amorphous shape thereof contribute greatly to the efficacy of the bone graft composition and to the porous microstructure of the cured material resulting therefrom.

Samples of small amounts of dry powdered composition, such as the exemplary formulation A1, were sprinkled on sticky carbon tape on aluminum sample holders. The samples were sputtered with carbon and a top layer of gold to a total thickness of approximately 20 nm. Zeiss MA 25 Scanning electron microscope was used with instrument settings chosen per each specimen in order to provide optimum image quality. Several images were captured at different locations on each sample, and the magnifications were matched to the particle size.

Setting Time and Temperature:

The setting time and heat emission (evaluated by following the temperature fluctuations in the immediate surrounding) of the setting reaction of the bone graft composition presented herein, such as the exemplary formulation A1, were determined. The setting time of an injectable cementitious paste determines the work flow during application and is thus of utmost importance to be well defined and to correspond to the specifications given in the application instructions. Ideally, a cementitious bone graft composition provides an open working time frame after mixing of up to several minutes, followed by a short setting reaction. However, the heat released by exothermic setting reactions can cause inflammations in the surrounding tissue, and the faster the setting proceeds, the higher the temperature rises. The maximum reaction temperature is thus limited in order to maintain biocompatibility of the product.

Exothermic heat was tested using polytetrafluoroethylene molds (international standard ASTM F 451-99a), fitted with THERMOCONTROL® TKI20/50FIM.K, Type K thermocouples.

Data logger used was Center 309 Datalogger.

Paper wipes used were VWR® Spec-Wipe® 3 Wipers, Polyester/Cellulose blend wipers, Size 23×23 cm, VWR North American Cat. No. 21914-758, European Cat. No. 115-0031.

Aqueous solution used was TEVA Medical Sodium Chloride 0.9% for IV injection.

Prior to the test series, two thermo couples were equilibrated at 0° C. in thermally stable ice water. The sampling frequency was set to 0.2 Hz. The test was started once the empty test setup had reached ambient temperature.

The setting time was measured as follows:

15 grams of a dry powdered bone graft composition, such as formulation A1, were placed on a large piece of standard paper wipe to allow excess saline to drain and be squeezed out without loosing the form of the setting sample;

25 ml of the aqueous solution (saline) were prepared in order to form a paste, and data recording started as soon as the aqueous solution was added to the powder;

The paste was kneaded gently until complete wetting was achieved, and excess liquid was squeezed out;

The kneaded paste was transferred into a designated mold, which was sealed immediately using clamps to press the lid onto the mold and squeeze out excess air and cement paste;

Data was recorded for 30 minutes from initial paste preparation.

The setting time and reaction temperature were calculated from the recorded data according to ASTM F451-99a.

Volumetric Porosity:

The volumetric porosity of a cured sample of a bone graft composition as presented herein was determined by gravimetry (measurement of weight or density). The quantitative calcium sulfate form content of the composition, determined by X-ray diffraction as described hereinabove, was required for the gravimetric calculations. Cured samples were prepared as described in the compression strength test hereinabove. True density is the density of a porous solid defined in the art as the ratio of its mass to its true volume. The density of a matter, which is essentially composed of a powder or particulate solid, in contrast to bulk density of a matter, is determined as the average density of a large volume of the powder in a specific medium (usually air) [Van Keulen, J., "Density of porous solids", *Materials and Structures,* 1973, 6(3), pp. 181-183]. The true density of the samples was determined as follows:

The weight of each cylindrical sample ($\pm 0.1$ mg) was recorded as M1 in grams;

The height of each sample ($\pm 0.02$ mm) was recorded as M2 in cm;

The diameter of each sample ($\pm 0.02$ mm) was recorded as M3 in cm;

The volume was calculated as M4..$\pi$M2 in cubic cm;

The true density was calculated as M5=M1/M3 grams per cubic cm.

The theoretical density depends on the phase composition as determined by quantitative XRD analysis.

The theoretical densities of the individual components were taken from the PDF-4+ data base $\rho_{CSD}$ ($\rho$, the Greek letter rho, stands for density, and $\rho_{CSD}$ denotes density for CSD): 2.310 grams per cubic cm (PDF #04-009-3817, $\rho_{CSH}$: 2.733 grams per cubic cm (PDF #00-041-0224, $\rho_{CSA}$: 2.961 grams per cubic cm (PDF #04-007-6682. The theoretical density of the sample, denoted M6, was calculated as M6=$W_{CSD}$ $\rho_{CSD}$+WCSH $\rho_{CSH}$+$W_{CSA}$ $\rho_{CSA}$. The volumetric porosity V was calculated as V=100(1−M5/M6). Twenty seven samples were used to calculate the mean value and the standard deviation.

SEM Analysis of Cured Samples:

The resorption rate of synthetic bone substitute implants is not only influenced by the chemical composition of the implant material, but also by the porosity, the specific surface area, and the shape and size of the crystallites. Ideally, randomly oriented and strongly intergrown crystals provide a framework with consistent and isotropic mechanical stability, a high specific surface area, and an open porosity to allow fluid infiltration and circulation. In this study, the microstructure of an exemplary cured bone graft composition was visualized by scanning electron microscopy (SEM).

Cured samples of bone graft composition, such as the exemplary formulation A1 (Bond Bone™) were prepared according to the pre-application procedure described herein, as well as in the instructional video provided to the practitioner and available on-line (internet sites). The resulting wet and pliable cementitious paste was extruded into cylindrical metallic molds of 9.5 mm ($\pm 0.5$ mm) in diameter and 9.5 mm ($\pm 0.5$ mm) height. The molds were tempered at 37° C. from the beginning of the preparation to the extrusion of the specimen. After injection the molds were covered with a wet tissue and stored at 37° C. for 1 hour. Thereafter the samples were sanded to the exact height of the molds and then extruded. Each specimen was placed in a cavity of a cell-culture well plate. The well plate was closed with a lid in order to prevent evaporation. After 24 hours at 37° C. the specimens were dried at ambient conditions (21$\pm 1$° C., 40$\pm 5$% relative humidity) for 24 hours and in an exsiccator at room temperature for at least 48 hours. The samples were then let at ambient conditions for at least 24 hours to be in equilibrium with ambient humidity and temperature. A sample was broken normal to the cylinder axis, and sputtered with carbon and a top layer of gold to a total thickness of approximately 20 nm. A Zeiss MA 25 Scanning electron microscope was used with instrument settings chosen per each specimen in order to provide optimum image quality. Several images were captured at different locations on each sample at low resolutions in order to show an overview of the sample, and at higher resolutions to show details of peripheral and core zones. The magnifications were matched to the particle size.

Experimental Results

Characterization of Formulation A1 (Bond Bone™):
Purity:

The purity analysis of the dry powder of the exemplary bone graft composition referred to herein as formulation A1, was obtained as described hereinabove using inductively coupled plasma (ICP) combined with atomic absorption spectroscopy (AAS) and atomic fluorescence spectroscopy (AFS), and the results are presented in Table 3 below:

TABLE 3

| Element | Symbol | Value (ppm) | Method |
|---|---|---|---|
| Lead | Pb | <1.5 | AAS |
| Cadmium | Cd | <0.2 | AAS |
| Mercury | Hg | <0.2 | AFS |
| Arsenic | As | <2 | AAS |
| Iron | Fe | 14.0 | ICP |

As can be seen in Table 3, the goal concentration of trace elements in the pre-set bone graft composition of less than 10 ppm of total heavy metals trace for Pb, Cd, Hg and As was reached. The iron concentration (14.0 ppm) was found to be below the accepted limit of 100 ppm. These values are generally acceptable for use in medical procedures according to ASTM F 2224-03.

Compressive Strength:

The results of the compressive strength and elastic modulus analysis, obtained for individual cured samples of the exemplary bone graft composition formulation A1 are presented in Table 4 below:

TABLE 4

| Sample No. | Compressive strength (MPa) | Elastic modulus (MPa) |
|---|---|---|
| 1 | 7.76 | 556 |
| 2 | 9.59 | 705 |
| 3 | 5.62 | 579 |
| 4 | 8.39 | 622 |
| 5 | 7.90 | 525 |
| 6 | 7.14 | 494 |

Table 5 below presents the average compressive strength and elastic modulus of cured samples of formulation A1.

TABLE 5

| Average compressive strength | 8 MPa |
|---|---|
| Standard deviation | 1 MPa |
| Average elastic modulus | 580 MPa |
| Standard deviation | 76 MPa |

As can be seen in Tables 4 and 5, the average compressive strength of the cured samples is in the expected range for non-sintered ceramics in general and other manually prepared calcium sulfate based products in particular, such as DentoGen™ LaserLok™ and the likes. The standard deviation observed is as well common for such materials and it reflects the high variations inherent to ceramic products, as well as variations induced by the manual preparation of the product. The stiffness (E-modulus) is similar to other known calcium sulfate-based bone graft products.

Particle Size Distribution:

Table 6 below presents the measured particle size distribution obtained for formulation A1.

TABLE 6

| Mesh [μm] | M1 [g] | M2 [g] | M3 [g] | M4 [wt-%] |
|---|---|---|---|---|
| collector | 339.54 | 337.89 | 1.65 | 1.66 |
| 32 | 268.9 | 262.54 | 6.36 | 6.41 |
| 53 | 244.00 | 233.86 | 10.14 | 10.22 |
| 106 | 264.93 | 246.28 | 18.65 | 18.81 |
| 250 | 296.80 | 267.11 | 29.69 | 29.94 |
| 500 | 305.63 | 292.85 | 12.78 | 12.89 |
| 710 | 328.17 | 317.57 | 10.60 | 10.69 |
| 1000 | 330.83 | 321.85 | 8.98 | 9.06 |
| 1400 | 332.1 | 331.78 | 0.32 | 0.32 |
| 2000 | 0.00 | 0.00 | 0.00 | 0.00 |

Figure 2:
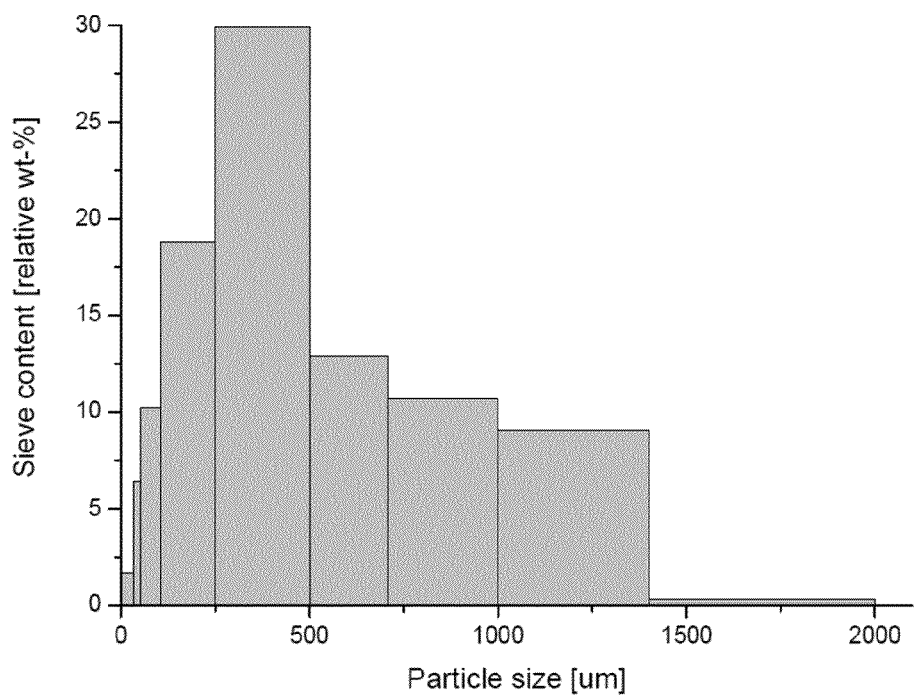
FIG. 2 presents a bar graph, showing the particle size distribution analysis obtained for a sample of dry powder of formulation A1, an exemplary bone graft composition according to some embodiments of the invention.

FIG. 2 presents a bar graph, showing the particle size distribution analysis obtained for a sample of dry powder of formulation A1 and presented in Table 6.

Figure 3:
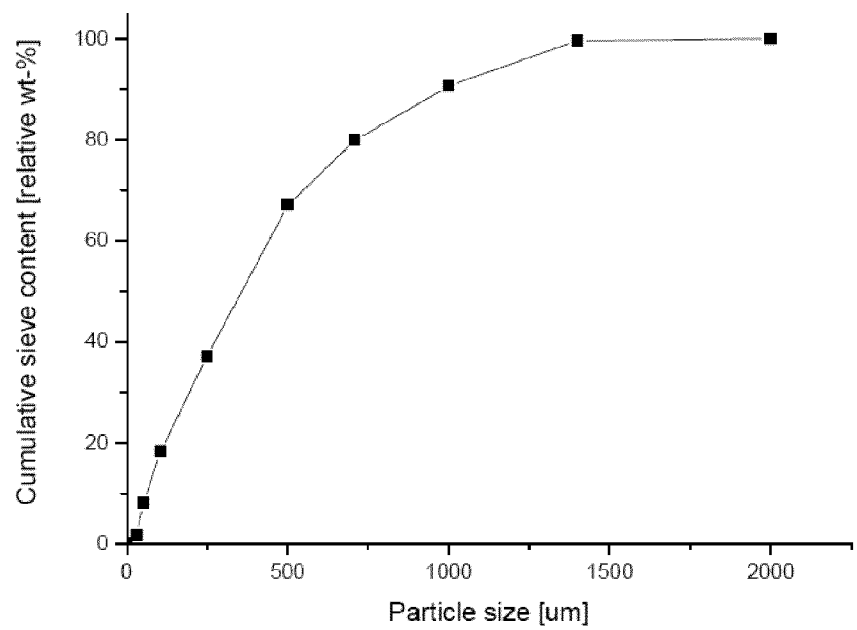
FIG. 3 presents a plot, showing the cumulative representation of the particle size distribution obtained for a sample of dry powder of formulation A1, an exemplary bone graft composition according to some embodiments of the invention.

FIG. 3 presents a plot, showing the cumulative representation of the particle size distribution obtained for a sample of dry powder of formulation A1 and presented in Table 6.

The sieving process alters the size of particle and agglomerates thereof, thereby altering the particle size distribution, since ensuring complete sieving may also break down weak particles and particle agglomerates. As can be seen in Table 6 and FIGS. 1 and 2, the material seems to be free of sub-micron particles. The fraction caught in the collector pan (<32 μm) is less than 2% by weight, and the larger agglomerates are in the range between 100 and 700 μm.

Calcium Sulfate Hydration Form Content:

Table 7 below presents the results of the phase composition analysis obtained for three individual dry powder samples (upper lanes) and three individual cured samples (upper lanes) of formulation A1.

TABLE 7

| Sample | CSD [wt-%] | CSH [wt-%] | LiF [wt-%] |
|---|---|---|---|
| Powder 1 | 34 ± 2 | 32 ± 2 | 35 ± 2 |
| Powder 2 | 32 ± 2 | 34 ± 2 | 34 ± 2 |
| Powder 3 | 32 ± 2 | 35 ± 2 | 33 ± 2 |
| Cured 1 | 65 ± 2 | 1 ± 1 | 33 ± 2 |
| Cured 2 | 67 ± 2 | 1 ± 1 | 32 ± 2 |
| Cured 3 | 67 ± 2 | 1 ± 1 | 32 ± 2 |

Table 8 below presents the average phase composition and calculated amorphous contents of formulation A1 prior to and after setting.

TABLE 8

| Sample | CSD [wt-%] | CSH [wt-%] | amorphous [wt-%] |
|---|---|---|---|
| Powder blend | 41 ± 2 | 42 ± 2 | 16 ± 2 |
| Cured | 88 ± 2 | 2 ± 1 | 11 ± 2 |

As can be seen in Tables 7 and 8, essentially all the CSH is converted to CSD during the setting process. Due to the high absorption contrast between the different hydration forms of calcium sulfate (phases) and the internal standard powder, a correction for micro-absorption had to be performed after the refinement. The calculation of the Brindley coefficient is based on the average particle radius of each form of calcium sulfate, and is estimated herein.

pH Analysis:

Table 9 below presents the results of two pH measurements obtained for the incubation solution of formulation A1, an exemplary bone graft composition, stabilized after stirring for about 12 hours.

TABLE 9

| Measurement | pH value | Temperature [° C.] |
|---|---|---|
| 1 | 7.62 | 24.1 |
| 2 | 7.76 | 24.5 |
| Average | 7.69 | 24.3 |

As can be seen in Table 9, the pH values were essentially neutral during the initial 12 hours of incubation; however, the pH is expected to change during resorption.

Figure 4A:
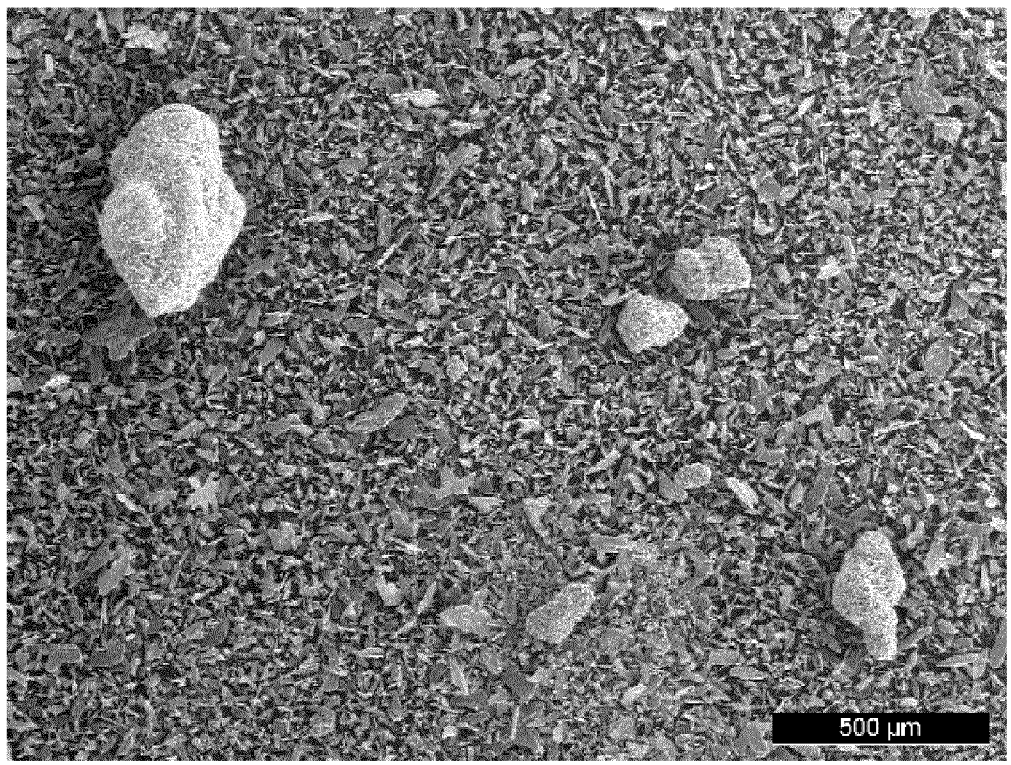
FIGS. 4A-C are scanning electromicrographs of a sample of formulation A1, an exemplary bone graft composition according to some embodiments of the invention, showing recognizable agglomerates at magnifications of 50-fold, 100-fold and 500-fold respectively.
Figure 4B:
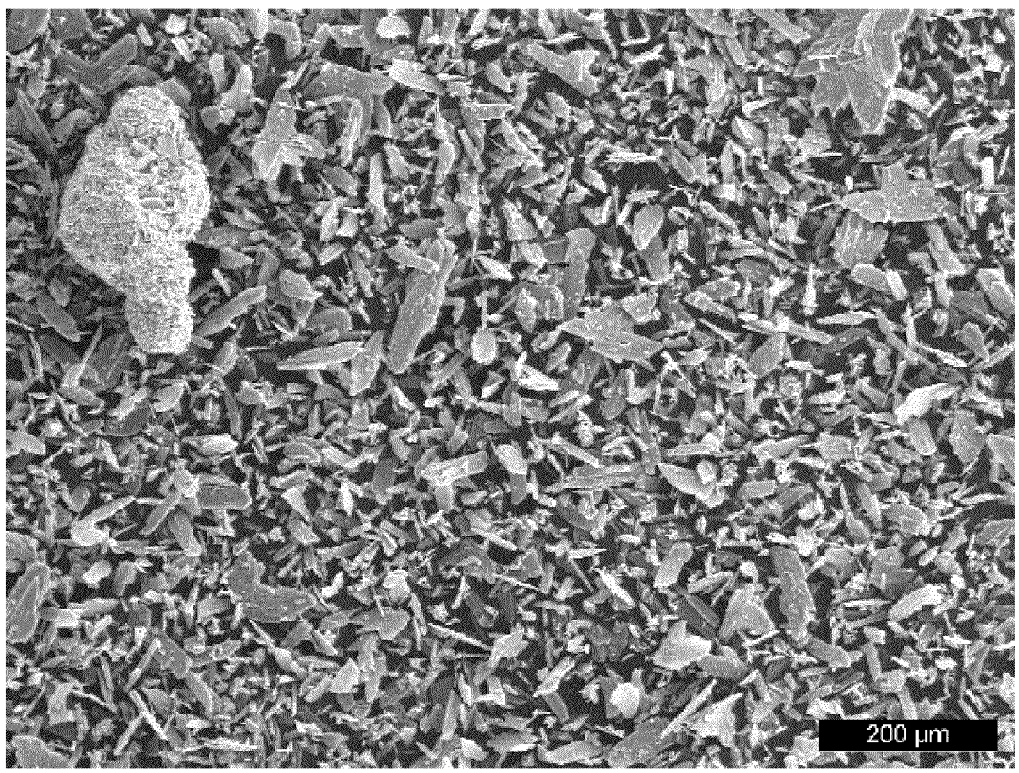
Figure 4C:
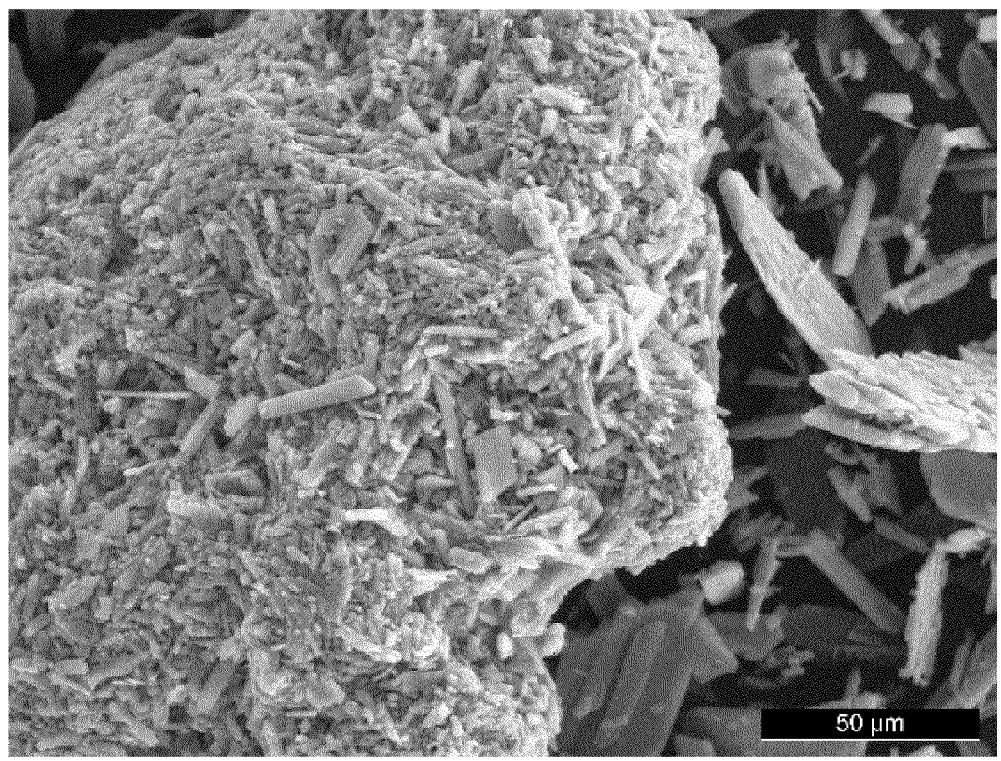

SEM Analysis of Particle Morphology:

SEM images of the dry powder samples of formulation A1 are shown in FIGS. 4A-C. FIGS. 4A-C are electromicrographs showing recognizable agglomerates at magnifications of 50-fold, 100-fold and 500-fold respectively.

As can be seen in FIGS. 4A-C, the particles exhibited mainly plate-like or needle-like morphology, while particle aggregates assumed a more sphere-like morphology. The size range was quite wide, with very fine particles of about 1 μm which were dispersed between larger particles of about 50-100 μm. Aggregates which were observed as composed of very fine particles measured up to 500 μm and larger. No differences were observed between different samples.

Setting Time and Temperature:

As mentioned hereinabove, the setting time of injectable bone cement should allow the practitioner a reasonable working time frame of several minutes, followed by a short setting reaction, as well as a minimal heat release as a result of the setting time in order to refrain from patient discomfort and inflammations in the surrounding tissue. The setting time was determined according to the short method presented hereinabove.

Formulation A1 was subjected to the aforementioned setting procedure, and experience has shown that injection and modeling of an implant body based on the same formulation is still possible for some time after the reported setting time.

Figure 5:
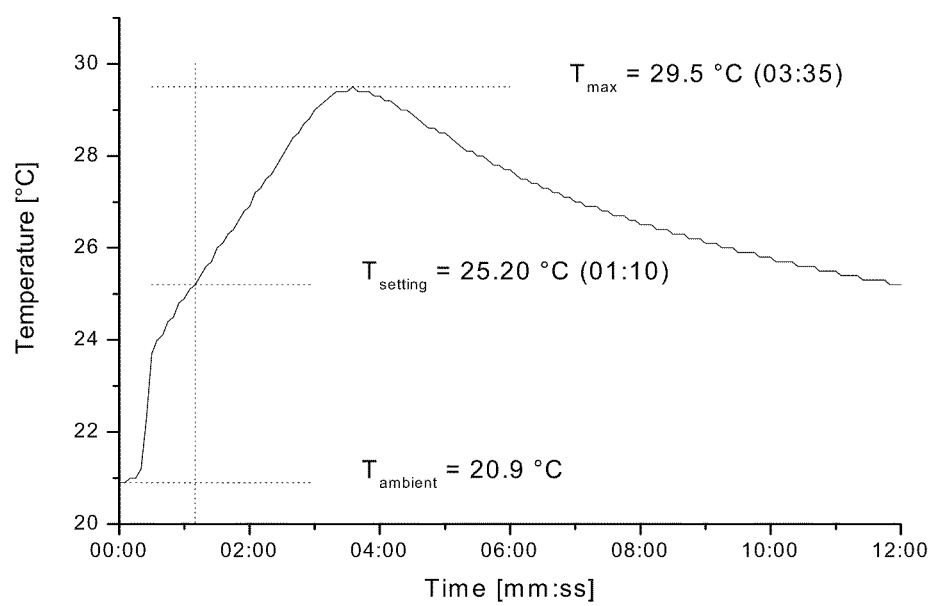
FIG. 5 presents a plot of temperature versus time as measured for a sample of formulation A1, an exemplary bone graft composition according to some embodiments of the invention, showing that heat release is detected immediately after mixing, and reaches a maximal average reaction temperature of 29.4 (±0.9)° C. after 3:34 (±00:04) minutes in average, with an average setting time of 1:12 (±00:05) minutes.

FIG. 5 presents a plot of temperature versus time as measured for a sample of formulation A1, an exemplary bone graft composition according to some embodiments of the invention, showing that heat release is detected immediately after mixing, and reaches a maximal average reaction temperature of 29.4 (±0.9)° C. after 3:34 (±00:04) minutes in average, with an average setting time of 1:12 (±00:05) minutes.

As can be seen in FIG. 5, although the heat release and perceived/measurable temperature depends on the preparation method and the heat capacity of the plunger device, the recorded maximal temperature was far below the maximum value allowed for acrylic bone cements, which according to ASTM F 451-99a can be as high as 90° C.

Volumetric Porosity:

The average true density was measured according to the procedure presented hereinabove, and the value obtained for M5 was 1.25±0.02 grams per cubic centimeter (cc).

The phase composition determined by XRD was 98.22% weight percentages for $W_{CSD}$, 1.78% weight percentages for $W_{CSH}$. Therefore, the calculated average volumetric porosity was 46±1%.

SEM Analysis of Cured Samples:

Low magnification images were taken in order to obtain an overview showing the peripheral and inner zones of a fracture surface. Detail images of increasing resolution of the peripheral zone are shown in FIGS. 6A-D.

Figure 6A:
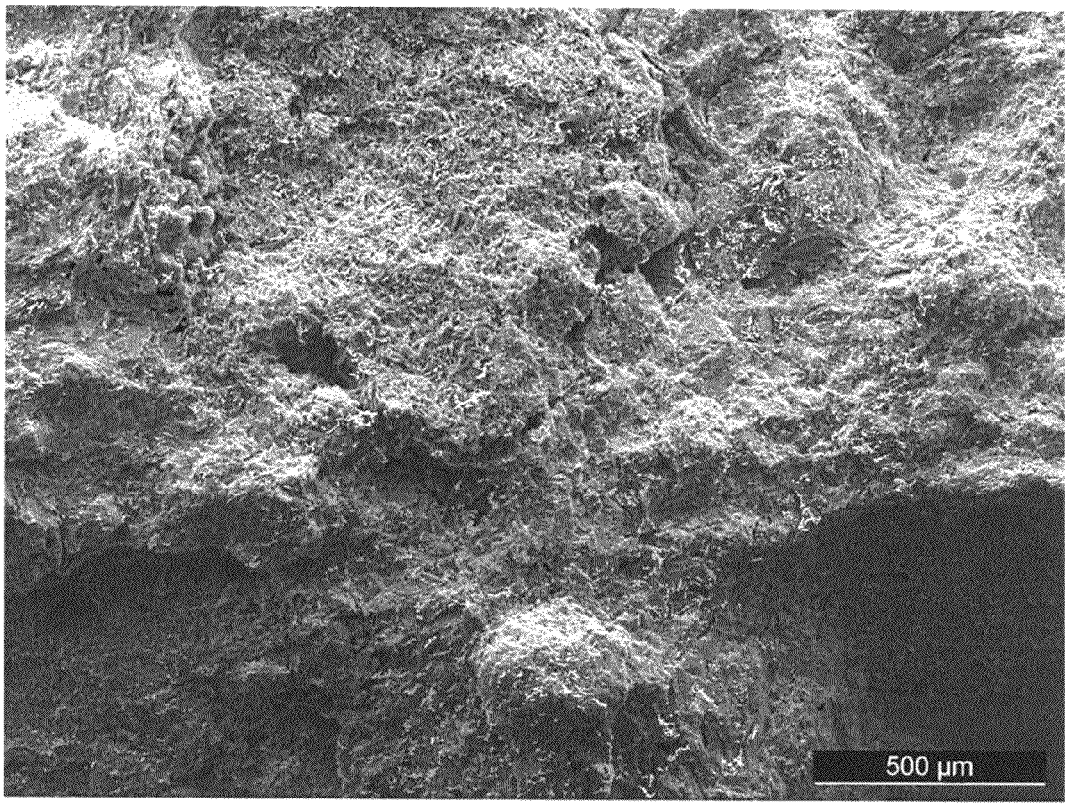
Figure 6B:
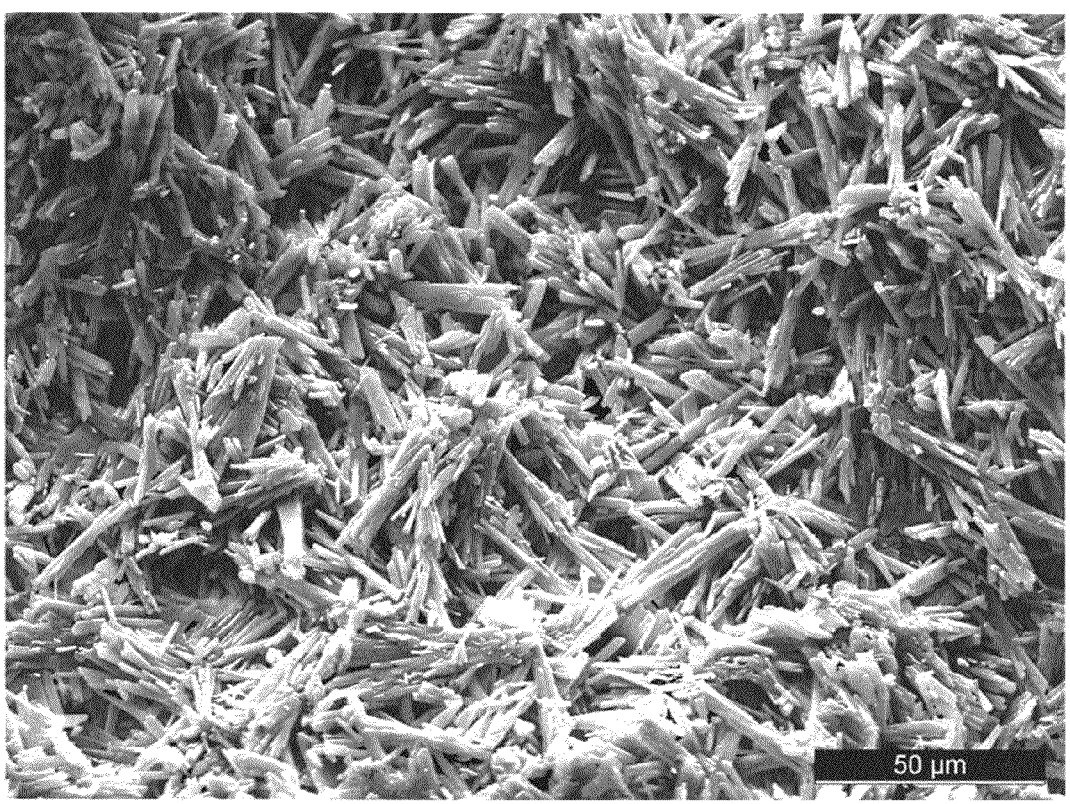
Figure 6C:
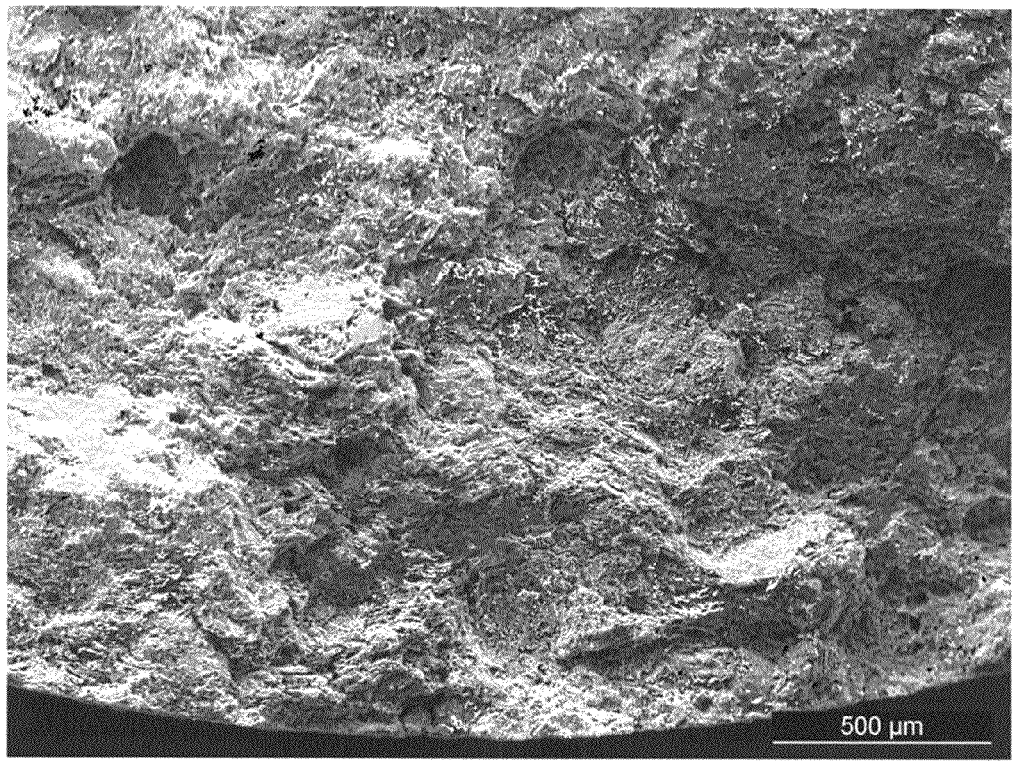
Figure 6D:
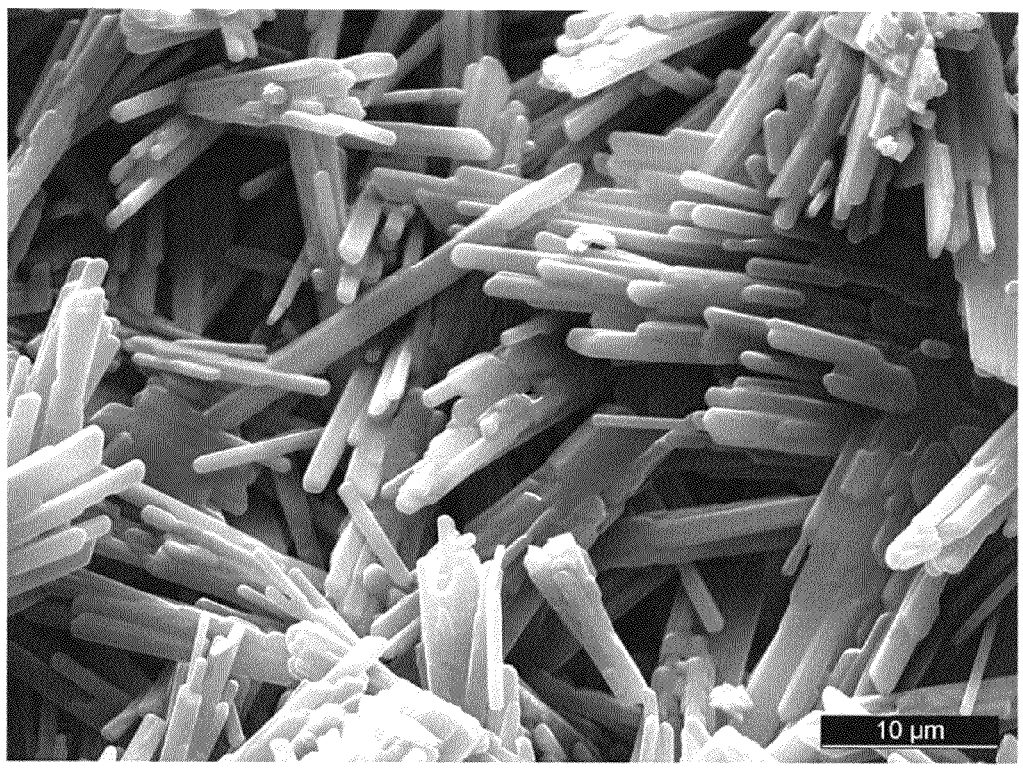

FIGS. 6A-D are scanning electromicrographs at different magnifications, taken at different locations of a cured sample of formulation A1, an exemplary bone graft composition according to some embodiments of the invention, in its post-activation and post-curing form, whereas FIG. 6A is taken from a core location at 50-fold magnification and FIG. 6B of the same location taken at 500-fold magnification, and FIG. 6C is taken from a peripheral location at 50-fold magnification and FIG. 6D of the same location taken at 2000-fold magnification, whereas FIG. 6A and FIG. 6C show an overall rough and uneven microstructure of the bulk structure, exhibiting large amorphous pores (pore diameter ranging from 300 µm to 800 µm), and whereas at higher magnifications FIG. 6B shows the micro-pores between CSD crystals, and FIG. 6D shows the needle-shaped strongly intergrown crystals of CSD which determine the porous fine microstructure comprising pores of various sizes and shapes.

As can be seen in FIG. 6A-D, there are no substantial differences between the peripheral and core locations in the samples. The low magnification micrographs reveal a fractured surface of a brittle cured concrete, which appears uneven and porous, as it is expected from a sample without a preferred cleavage planes, while the high magnifications images reveal a porous micro-structure composed of randomly oriented or bundled intergrown needle-like crystals of about 1-50 µm in length.

As can be discerned from the electromicrographs, the cured solid obtained from the bone graft composition presented herein, is characterized by macro- and micro-pores which form during the setting and curing process thereof due to the original chemical composition and particle size distribution of the bone graft composition. The micro-structure observed in the electromicrographs explains the high degree of porosity of 50% by volume, as calculated by density measurements. It is also reasonable to expect good infiltration properties due to capillary forces.

Therefore, the porous and irregular microstructure, effected by the initial variation in particle size and shape, provides a unique balance between the mechanical properties, bio-resorption period and beneficial biologic effects, such as permeability to physiological media, growth factors and bone regeneration cells, which are essential for a proper bone reformation.

Characterization of Formulation B:

In another embodiment of the invention, a bone graft composition, composed of a combination of highly-resorbable substances and poorly-resorbable substances, provided a granule-reinforced bone grafting matrix exhibiting characteristics which are highly desirable in various medical procedures. This family of compositions was based on cementitious and highly-resorbable particles, reinforced with highly-resorbable particles as well as poorly-resorbable particles made of various substances. The process for obtaining the bone graft composition according to this embodiment included pre-mixing the particles of the non-cementitious substance(s) with CSH particles to thereby obtain coating of the non-cementitious with a layer of CSD upon hydration. The reinforcing calcium sulfate and other particles of poorly-resorbable, such as, without limitation β-TCP, Cerabone® Bio-Oss® grains, created a composite matter with very good mechanical properties, and the overall hardness of the composite was significantly higher than that of the calcium sulfate matrix.

Figure 7A:
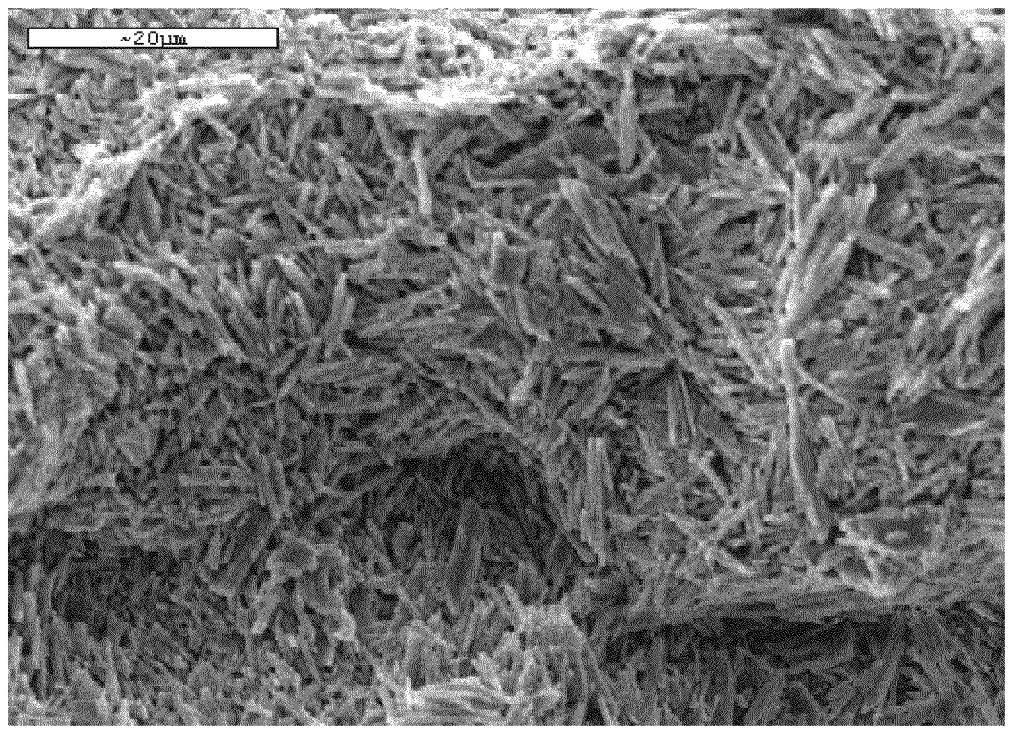
Figure 7B:
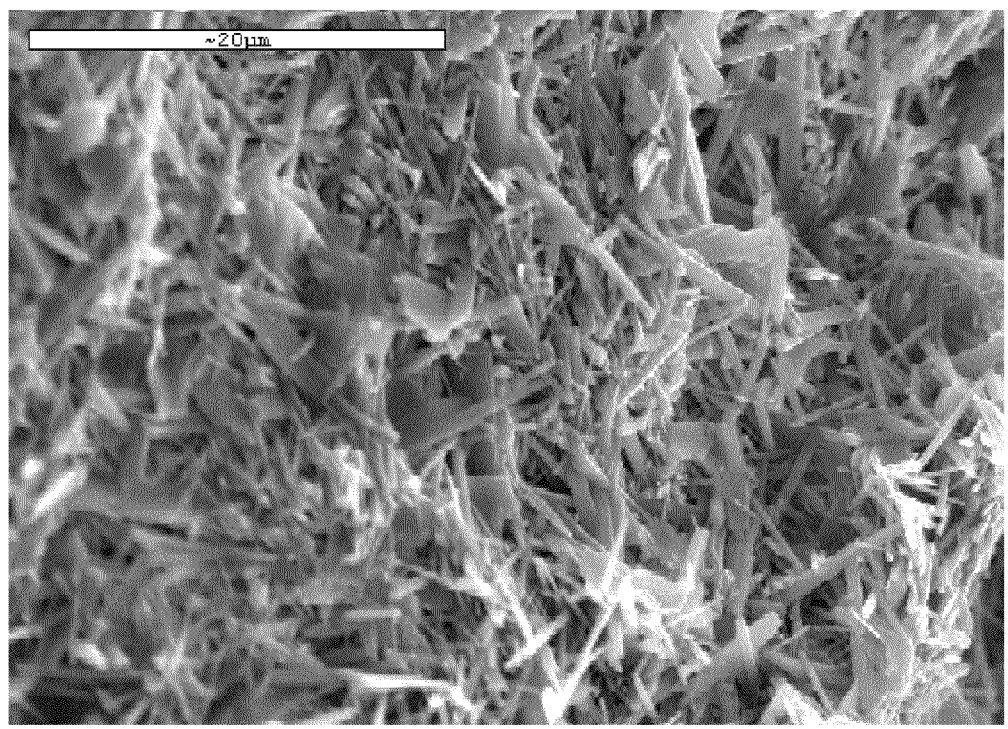
Figure 7C:
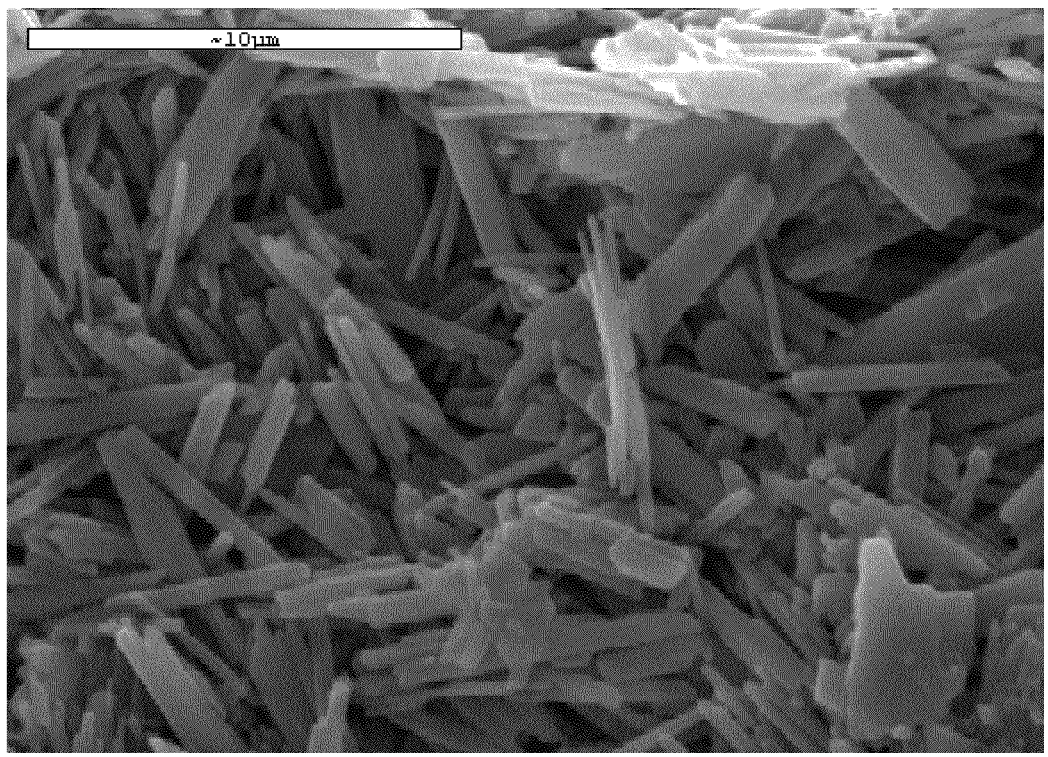

SEM Analysis of Cured Samples:

FIGS. 7A-C are electromicrographs of cured samples of formulation B, wherein FIG. 7A is a micrograph at a magnification of 1500-fold, FIG. 7B is a micrograph at a magnification of 2500-fold and FIG. 7C is a micrograph at a magnification of 5000-fold, showing a similar microstructure as obtained for the cured samples of formulation A.

As can be seen in FIG. 7A-C, a plurality of small crystallites composed of randomly oriented needle-shaped and highly intergrown crystals is observed in the cured samples. This microstructure is utilizing a composition of which a major part is composed of non-cementitious and insoluble CSD particles before the setting process begins. Therefore, a bone graft composition containing relatively large particles of CSD and rigid β-TCP crystals, engulfed in a continuous "phase" of CSH, is expected to improve the mechanical properties and delay the degradation period of the graft.

Packaging, Activation and Application Device

The bone graft compositions presented herein can be provided to the practitioner in bulk, in pre-weighted and individually-packed doses, or in pre-loaded applicators, or drivers, containing a pre-weighted dose of the composition.

For example, formulation A1, an exemplary bone graft composition according to some embodiments of the invention, which is also referred to herein as "Bond Bone™" can be provided to the user in different applicator sizes, pre-packed with the dry composition, such as, for example a small applicator containing 0.5 cc (about 0.63 grams), and in a large driver containing 1 cc (about 1.25 grams).

Figure 8A:
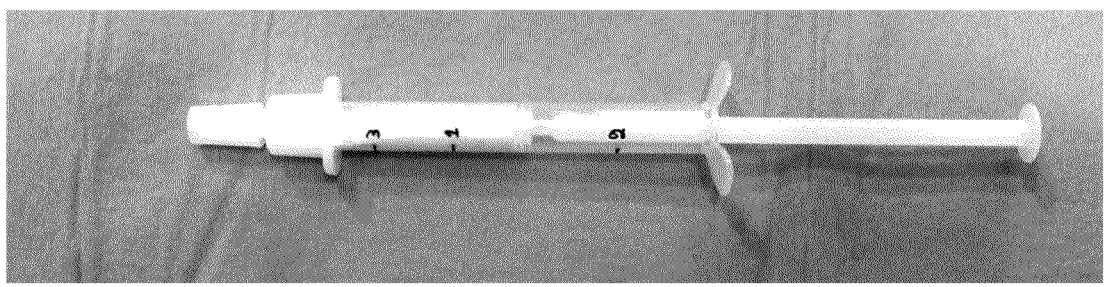
Figure 8B:
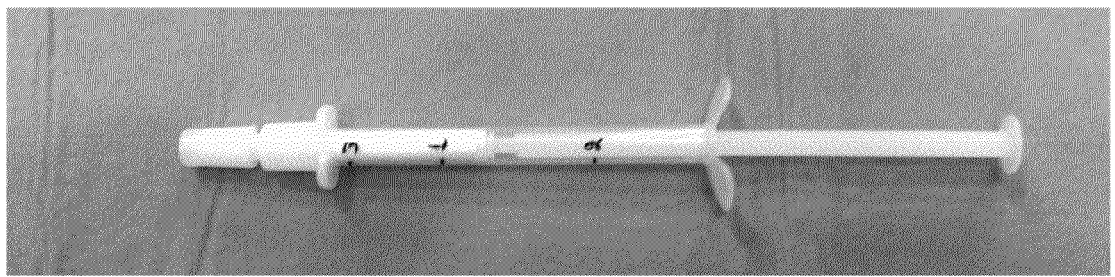

FIGS. 8A-B are photographs of an exemplary applicator device according to some embodiments of the invention, composed of four basic elements, namely a cylindrical tube, a piston assembly, a tubular applicator's head and a cap fabricated from certified biocompatible raw materials that withstand gamma radiation according to ISO standards, designed to contain the bone graft composition according to the present embodiments, and eventually apply the same, wherein FIG. 8A shows an applicator for a small dose of 0.5 cc (about 0.63 grams) of dry bone graft composition, and FIG. 8B shows a larger size applicator containing 1 cc (about 1.25 grams) of the composition.

The elements of the exemplary applicator shown in FIGS. 8A-B are described in Table 10 below.

TABLE 10

| Element | Function | Material | Reference in FIG. 1 |
|---------|----------|----------|---------------------|
| Cylindrical tube | Store and deliver the bone graft composition | Medical grade polypropylene Purell HM671T | Tube 12 |
| Piston | Draw liquid into the tube to wet the composition and start the setting reaction, and push the resulting paste onto the implantation site | Medical grade polyethylene Purell 5037L | Piston assembly 13 |
| Applicator's head | Reduce outer diameter for in-flow of wetting liquid and a gauge adaptor tor for a standard syringe needle in cases where a septum-sealed aqueous solution container | Medical grade polyethylene Purell 5037L | Head 30 |
| Cap | Cover driver opening to prevent spill of the powder or paste | Medical grade polyethylene Purell 5037L | Cap 18 |

The materials for the applicator's parts were purchased from LyondellBasell Company (The Netherlands), and the parts were fabricated by contract at 3BY Medical Devices Ltd. (Tefen, Israel).

As presented hereinabove, the design concept of an applicator according to some embodiments of the invention is illustrated in FIG. 1. As can be seen in Table 10, all the components of the applicator are based on certified biocompatible raw materials that withstand gamma radiation, fabricated by ISO certified producers. Each of the components can be made independently, and without limitation, from a variety of suitable polymeric materials, coated plastics, fluorinated resins, glasses and any combinations thereof.

The applicator is therefore used to hold the dry powdered bone graft composition, activate and deliver it during implantation. In the first stage it is used to draw a liquid from an external reservoir into the piston using the applicator's head with or without an additional needle that can be connected to the applicator's head. Once a liquid is drawn into the piston, thereby wetting the composition, the material begins its setting reaction. Thereafter, the user disconnects the applicator's head and applies the resulting paste out of the applicator and into the application site. After application the applicator can be disposed. A detailed and illustrated directive procedure for using an applicator according to the present embodiments is presented hereinbelow.

To ensure optimal and reproducible results and simplify the use of the applicator, three lines are printed on the applicator's tube (tube 12 in FIG. 1), which are numbered in print according to the order of actions in the overall procedure of preparing and applying the composition, as detailed below. Table 11 below presents the distance of the lines from the aperture of the cylindrical tube (aperture 20 in FIG. 1) as marked on two exemplary applicators according to the present embodiments, a 1 cc applicator and a 0.5 cc applicator.

TABLE 11

| Line No. | Reference in FIG. 1 | Distance from aperture in a 1 cc applicator [mm] | Distance from aperture in a 0.5 cc applicator [mm] |
|---------|---------------------|---------------------------------------------------|---------------------------------------------------|
| 3 | third line 23 | 17 | 14 |
| 1 | first line 21 | 32 | 31 |
| 2 | second line 22 | 63 | 61 |

Practical Composition Application

The bone graft compositions presented herein are indicated for use by themselves in bone regeneration procedures; and/or mixed with other suitable bone filling agents to prevent particle migration in an osseous defect; and/or to provide a resorbable barrier over other bone graft material.

The bone graft compositions presented herein can be stores at temperatures between 5° C. (41° F.) to 30° C. (86° F.), and preferably away from heat sources or direct sunlight. The compositions can be provided as granulated powder in bulk or in pre-weighted containers, or as pre-weighted doses packed within an application, such as the applicator described herein.

The following is a description of an exemplary mode of application of the compositions provided herein using the exemplary applicator described herein and illustrated in FIG. 1 and FIGS. 8A-B.

Prior to use, a suitable sterile aqueous solution, such as a sterile standard saline (0.9% sodium chloride for injection) is required on-site as a wetting and setting agent. The bone grafting site in the subject of the treatment is prepared by removing the undesired soft tissue from the exposed bone surface and preparing the defected area for bone augmentation procedure.

The procedure for preparing the bone graft composition includes eleven basic steps. It is recommended that the time elapsed from the encounter of the composition with the aqueous solution would not exceed two minutes, since the material will lose his pliability and malleability. The following description may be better understood with reference to the accompanying FIGS. 9A-J, each of which is referred to according to its relevance within the description.

Figure 9A:
FIGS. 9A-J, are photographs which form a part of an instruction document for the use of an applicator device according to some embodiments of the present invention, designed for storing, preparing and applying a bone graft composition according to some embodiments of the present invention, as presented in details hereinbelow.
Figure 9B:
Figure 9C:
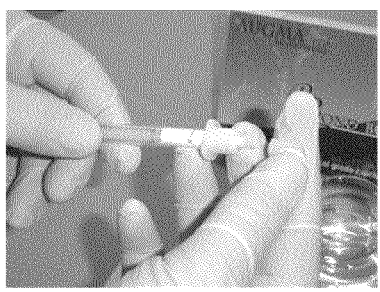
Figure 9D:
Figure 9E:
Figure 9F:
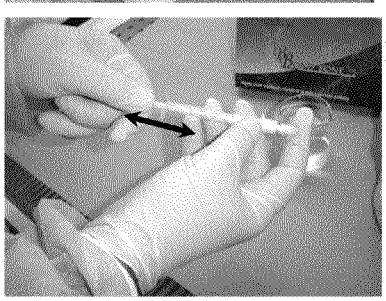
Figure 9G:
Figure 9H:
Figure 9I:
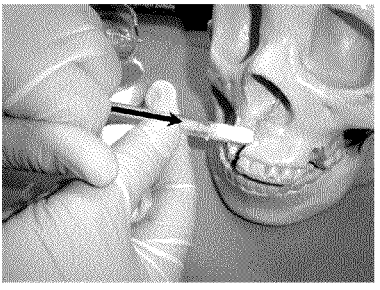
Figure 9J:

Before applying the composition, it is required to prepare the applicator filled with the required amount of the composition, a container filled with at least 5 cc of sterile aqueous solution such as saline (sodium chloride 0.9% for injection) and several dry and sterile gauze pads (FIG. 9A). The procedure is provided as a set of directive steps:

STEP 1: Hold the applicator (also referred to herein interchangeably as the driver) so that its head (head 30 in FIG. 1) will face upwards (FIG. 9B);

STEP 2: Tap the tube of the applicator (tube 12 in FIG. 1) with a finger, or any straight tool such a spatula, in order to disperse the dry composition;

STEP 3: Push the piston (piston 16 in FIG. 1) to line 1 marked on the applicator (first line 21 in FIG. 1);

STEP 4: Remove the applicator's small cap (cap 18 in FIG. 1), and keep within reach (FIG. 9C);

STEP 5: Pump aqueous solution into the applicator by slowly pulling the piston to line 2 (second line 22 in FIG. 1) while keeping the tip of the applicator's head is entirely immersed in the solution while pumping (FIG. 9D) and maintaining the applicator pointing down after pumping;

STEP 6: If the composition is not completely wet or at least humid by the solution, reconnect the cap, and while the applicator's head is facing down, tap on the applicator with a finger or a spatula (FIG. 9E), or move the piston back and forth while pressing the cap towards the applicator to blend the powder with the solution until a complete wetting is achieved (FIG. 9F);

STEP 7: Hold the applicator pointing upwards and remove the applicator's head (FIG. 9G), keeping the applicator in the same upwards position;

STEP 8: Cover the applicator's aperture with a folded dry gauze pad (or 2-3 pad stack) and press the pad firmly to the aperture with a finger. Allow excess solution to be expelled out by driving the piston, in a way that will prevent ejecting the resulting paste, to line 3 (third line 23 in FIG. 1) so as to remove liquid surpluses to thereby obtain the desired paste viscosity (FIG. 9H);

STEP 9: Use the applicator to apply the resulting pasty composition into the intended site by pushing the piston and ejecting the paste (FIG. 9I) while maintaining good contact between the paste and natural bone tissue and filling the bone defect entirely with the paste;

STEP 10: Apply a dry gauze pad for 3-5 seconds to condense the paste (FIG. 9J), and continue to shape the paste in its position in the bone defect as necessary to achieve the desired form; and STEP 11: Use a sterile solution such as saline to wet the gauze pad and place the wet pad above the graft for 30 seconds, and thereafter remove the gauze pad and proceed with soft tissue coverage and wound closure.

If a complete hardening of the paste prior to wound closer is required, the wet gauze is kept above the graft for 5 minutes before closure and suture.

It is noted herein that a membrane is not required in most surgical procedures when using the bone graft composition of the present embodiments. In addition, primary flap closure is recommended but not essential for proper healing, since soft tissue may grow on top of the applied and set composition. The present compositions can be used also as a membrane above other augmentation materials, in which case the same procedure presented above is applied over the selected augmentation material in a thickness which is not less then 1 mm.

DISCUSSION

Embodiments of the invention provide several unique bone graft compositions which are highly suitable for repairing bone defects by, for example, bone augmentation, and which include various and specific combinations of calcium sulfate particles in different solid forms (phases) that can, for example, harden in aqueous environment in a relatively short setting time without compromising patient comfort by heat or expansion.

In one embodiment, a particular combination of hydration forms of calcium sulfate in a particular particle size distribution ratio, as defined herein, provide a unique bone graft composition which exhibits an optimal setting and curing time, porosity, rigidity and bio-resorption period.

In another embodiment, the bone graft compositions include reinforcing materials which are currently used as dental and orthopedic bone grafts, mixed together with the calcium sulfate-based composition as defined herein.

The compositions provided herein provide strong hybrid bone graft materials which remain pliable for a sufficient time period, exhibit short setting times and afford a more rigid scaffold for bone grafts. The bone graft compositions presented herein produce structures which are less brittle than those produced by the known reinforcing materials due to the calcium sulfate-based matrix that is less rigid.

Various combinations of calcium sulfate hydration forms were developed on the basis of particular ratios of CSH and CSD, with or without CSA, thereby providing improved mechanical stability for longer duration. In addition, the unique porous structure and chemical composition determine the bio-resorption period that beneficially influences the bone regeneration rate. Several solid particle size distributions were analyzed in order to identify an advantageous particle size distribution which offered an optimal combination of mechanical properties, curing time, and pliability, leading to a more desirable, predictable and reproducible practical outcome.

In addition, the compositions presented herein may include other ingredients which affect the rate of degradation of the system while exposed to in vivo conditions, such as for example, CSA which can be added so as to slow biodegradation due to its slow resorption of water.

Therefore, formulation A1 (devoid of CSA), an exemplary bone grafting composition according to some embodiments of the invention, is recommended for systems which exhibit bio-resorption period of 4 to 10 weeks. Formulation B, another exemplary bone grafting composition according to some embodiments of the invention, which includes particles of other bone graft minerals that slow the resorption process of the matrix, is recommended for systems which require longer bio-resorption periods.

Following its cementitious reaction, formulation A1 maintained both volume and rigidity properties, and thus may function as a scaffold for bone regeneration. The SEM images presented herein indicated that crystallization produced of needle-like particles increased the strength of the cement. The morphology of the resulting structure is characterized by porosity of about 50%, made of a plurality of micro-pores which allow growth factor infiltration, and a plurality of macro-pores allow angiogenesis and bone tissue regeneration.

The compositions provided herein are characterized by an average bio-resorption rate that corresponds to bone generation rate at the selected bone defect. While osteoid formation occurs within the period of 6-10 weeks, bio-resorption period of existing bone grafting compositions is 4-6 weeks, whereas the resorption period of the exemplary formulation A1 is 4-10 weeks.

The exemplary formulation B described herein, is intended to produce a hybrid reinforced matrix material, or a composite bone grafting material, which combines good handling properties with short setting time and final rigidity, which is less brittle. This is achieved herein by coating currently known bone grafting materials with the unique calcium sulfate composition provided herein while maintaining a particular particle size distribution as defined herein. Achieving this goal was demonstrated by incorporating β-TCP particles with calcium sulfate particles. The reinforced calcium sulfate and β-TCP composites provided significantly high mechanical properties.

The reinforced calcium sulfate was also inspected using Cerabone®, which is a hydroxylapatite ceramic made of purely inorganic material that is supplied as a molding block in different sizes and as granules of differing dimensions, and Bio-Oss®, which is a natural osteoconductive bone substitute that consists of the mineral portion of bovine bone. These combined compositions exhibited very good mechanical properties without any reinforcing additives, such as polymers.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A bone graft composition comprising a plurality of particles of a cementitious substance and a plurality of particles of a non-cementitious substance, wherein the non-cementitious substance comprises calcium sulfate dihydrate and the cementitious substance comprises calcium sulfate hemihydrate, and wherein the plurality of particles of the non-cementitious substance is characterized by at least two non-overlapping ranges of particle size, the composition being characterized by a particle size distribution according to formula I:

$$T = a_0 S_0 + a_1 S_1 + a_2 S_2 + a_3 S_3 + a_4 S_4 + \ldots + a_i S_i + \ldots + a_n S_n$$

wherein:
T is the particle size distribution of the composition;
$S_0$ is the particle size range of the cementitious substance;
$a_0$ is a percentage by weight of the particles of the cementitious substance of the total weight of the composition;
i is an integer ranging from 1 to n;
n is an integer greater than 2;
$S_1, S_2, S_3, \ldots S_i \ldots S_n$ are each a particle size range of the non-cementitious substance;
at least two of $S_1, S_2, S_3, \ldots S_i \ldots S_n$ are non-overlapping particle size ranges;
$a_1, a_2, a_3, \ldots a_i$ are each a percentage by weight of the particles of the non-cementitious substance having $S_1, S_2, S_3, \ldots S_i$ particle size range of the total weight of the composition,
wherein:
when n=2:
$S_1$ is from 1000 μm to 2000 μm; and
$S_2$ is from 500 μm to 1000 μm,
when n=3:
$S_1$ is from 900 μm to 1800 μm;
$S_2$ is from 600 μm to 1200 μm; and
$S_3$ is from 200 μm to 600 μm, and
when n=4:
$S_1$ is from 800 μm to 1600 μm;
$S_2$ is from 500 μm to 800 μm;
$S_3$ is from 0 μm to 500 μm; and
$S_4$ is from 0 μm to 100 μm,
wherein the cementitious substance and the non-cementitious substance form a biocompatible concrete upon contacting a mixture thereof with an aqueous solution.

2. The composition of claim 1, wherein:
$S_0$ is from 0 μm to 500 μm;
$a_0$ is from 40 wt. % to 60 wt. % of the total weight of the composition; and
a sum of $a_1, a_2, a_3, \ldots a_i$ is from 40 wt. % to 60 wt. % of the total weight of the composition.

3. The composition of claim 1, wherein:
$S_0$ is from 0 μm to 100 μm and n=4;
each of $a_1$ and $a_3$ is from 15 wt. % to 18 wt. % of the total weight of the composition; and
each of $a_2$ and $a_4$ is from 7 wt. % to 10 wt. % of the total weight of the composition.

4. The composition of claim 1, wherein said non-cementitious substance further comprises a poorly-resorbable substance that exhibits a resorption time of more than 10 weeks.

5. The composition of claim 4, wherein the poorly-resorbable substance is selected from the group consisting of beta-tricalcium phosphate, hydroxylapatite, bovine-derived hydroxylapatite, porous coralline hydroxylapatite, calcified algae, synthetic particulate glass ceramic, bioactive glass, autogenic bone shavings, allogeneic cancellous bone, irradiated cancellous allogeneic bone, anorganic bovine bone, a polymer composite, calcium hydroxide and any combination thereof.

6. The composition of claim 1, wherein the non-cementitious further comprises beta-tricalcium phosphate.

7. The composition of claim 1, wherein:
$S_0$ is from 0 μm to 100 μm;
$a_0$ is about 50 wt. % of the total weight of the composition; n=4;
$S_1$ is from 800 μm to 1600 μm;
$S_2$ is from 500 μm to 800 μm;
$S_3$ is from 0 μm to 500 μm;
$S_4$ is from 0 μm to 100 μm;
each of $a_1$ and $a_3$ is independently about 16.5 wt. % of the total weight of the composition; and
each of $a_2$ and $a_4$ is independently about 8.5 wt. % of the total weight of the composition.

8. The composition of claim 6, wherein:
$S_0$ is from 0 μm to 100 μm;
$a_0$ is about 50 wt. % of the total weight of the composition; n=4;
$S_1$ is from 800 μm to 1600 μm;
$S_2$ is from 500 μm to 800 μm;
$S_3$ is from 0 μm to 500 μm;
$S_4$ is from 0 μm to 100 μm;
each of $a_1$ and $a_3$ is independently about 16.5 wt. % of the total weight of the composition; and
each of $a_2$ and $a_4$ is independently about 8.5 wt. % of the total weight of the composition.

9. The composition of claim 1, wherein the concrete is characterized by a setting time of from 1 minute to 1.5 minutes.

10. The composition of claim 9, wherein the concrete is pliable and malleable from 2 minutes to 4 minutes.

11. The composition of claim 1, present in a form of a physically discrete unit comprising a therapeutically effective amount sufficient to fill a bone defect.

12. The bone graft composition unit dosage form of claim 11, wherein the therapeutically effective amount is from 0.3 grams to 20 grams.

13. The composition of claim 11, wherein the physically discrete unit is a bone grafting applicator.

14. A method of repairing a bone defect, the method comprising:
contacting the bone graft composition of claim 1 with the aqueous solution, to form the concrete; and
applying the concrete to the site of the bone defect, thereby repairing the bone defect.

15. The method of repairing a bone defect of claim 14, wherein the contacting and/or the applying are performed using a bone grafting applicator.

16. The method of repairing a bone defect of claim 15, wherein the bone grafting applicator comprises:
- a cylindrical tube containing the bone graft composition and formed with an opening at one end thereof;
- a piston assembly including a piston moveable within the cylindrical tube, and a piston rod extending through the opposite end of the cylindrical tube and terminating in a finger-piece disposed externally of the cylindrical tube for moving the piston in opposite directions towards and away from the opening in the one end of the cylindrical tube; and
- a tubular head having one end dimensioned to be removably applied to the one end of the cylindrical tube to communicate with the opening therein, and an opposite end closed by a removable cap;
- the arrangement being such that, upon removal of the cap, the piston may be moved from a first position to a second position away from the opening in the cylindrical tube to draw the aqueous solution into the cylindrical tube and to mix with the bone graft composition therein to produce a biocompatible concrete, and the piston may be then moved towards the opening from the second position to a third position to force at least a portion of the aqueous solution, and further, upon removal of the tubular head, the piston may be moved towards the opening from the third position to force the biocompatible concrete via the opening to the site of a bone defect.

17. A method of applying a flowable mixture of the bone graft composition of claim 1 with a liquid carrier to a receiver site, the method comprising:
- placing an applicator, having a dry composition contained within a cylindrical tube, a piston at a first position, and a removable cap being removed, in a liquid carrier;
- while the applicator is placed in the liquid carrier, moving the piston to a second position, to thereby draw the liquid carrier into the cylindrical tube;
- shaking the cylindrical tube, so as to mix the dry composition and the liquid carrier, to thereby produce the flowable mixture;
- moving the piston to a third position so as to force at least a portion of the liquid carrier;
- removing the tubular head; and
- moving the piston towards the opening from the third position, to thereby force the flowable mixture via the opening to a receiver site, thereby applying the flowable mixture to the receiver site.

18. The method of claim 17, wherein the liquid carrier is an aqueous solution and the flowable mixture formed by mixing the bone graft composition and the aqueous solution is a biocompatible bone graft concrete, the method being for applying the concrete to a bone defect.

19. The method of claim 18, being for repairing the bone defect.

20. A process for preparing the bone graft composition of claim 1, the process comprising:
- providing a plurality of non-cementitious coarse particles having an average particle size that is from 0 to 1600 μm;
- dividing the plurality of non-cementitious coarse particles into $S_1, S_2, S_3, \ldots S_i$;
- providing the plurality of particles of the cementitious substance in $S_0$; and
- mixing $S_0$ and $S_1, S_2, S_3, \ldots S_i$ according to formula I.

* * * * *